(12) United States Patent
Wakui et al.

(10) Patent No.: US 11,331,933 B2
(45) Date of Patent: May 17, 2022

(54) CASSETTE AND SYSTEM

(71) Applicant: FUJITSU COMPONENT LIMITED, Tokyo (JP)

(72) Inventors: Takeshi Wakui, Tokyo (JP); Sumio Watanabe, Tokyo (JP); Masahiro Yanagi, Tokyo (JP); Toshiya Koyama, Tokyo (JP); Tatsuya Oguchi, Tokyo (JP)

(73) Assignee: FUJITSU COMPONENT LIMITED, Tokyo (JP)

( * ) Notice: Subject to any disclaimer, the term of this patent is extended or adjusted under 35 U.S.C. 154(b) by 335 days.

(21) Appl. No.: 16/438,959

(22) Filed: Jun. 12, 2019

(65) Prior Publication Data

US 2019/0381805 A1  Dec. 19, 2019

(30) Foreign Application Priority Data

Jun. 18, 2018 (JP) .............................. JP2018-115289

(51) Int. Cl.
| | |
|---|---|
| *B41J 3/36* | (2006.01) |
| *B41J 11/00* | (2006.01) |
| *B41J 13/02* | (2006.01) |
| *B41J 13/10* | (2006.01) |
| *B41J 29/393* | (2006.01) |
| *H04N 1/00* | (2006.01) |
| *H04N 1/32* | (2006.01) |

(52) U.S. Cl.
CPC ............... *B41J 3/36* (2013.01); *B41J 11/008* (2013.01); *B41J 13/02* (2013.01); *B41J 13/103* (2013.01); *B41J 29/393* (2013.01); *H04N 1/00397* (2013.01); *H04N 1/32* (2013.01); *H04N 2201/0096* (2013.01)

(58) Field of Classification Search
CPC ............. B41J 3/36; B41J 11/008; B41J 13/02
See application file for complete search history.

(56) References Cited

U.S. PATENT DOCUMENTS

| | | | |
|---|---|---|---|
| 6,238,043 B1 * | 5/2001 | Silverbrook | ........... G03B 17/02 347/86 |
| 6,416,160 B1 | 7/2002 | Silverbrook | |
| 6,553,459 B1 | 4/2003 | Silverbrook et al. | |
| 6,712,452 B1 | 3/2004 | Silverbrook et al. | |
| 6,804,026 B1 | 10/2004 | Walmsley | |
| 6,812,972 B1 | 11/2004 | Silverbrook et al. | |
| 6,903,766 B1 | 6/2005 | Silverbrook et al. | |

(Continued)

FOREIGN PATENT DOCUMENTS

| | | |
|---|---|---|
| CN | 204576078 U | 8/2015 |
| JP | S60-72430 U | 5/1985 |

(Continued)

OTHER PUBLICATIONS

Extended European Search Report dated Nov. 7, 2019 issued with respect to the corresponding European Patent Application No. 19180119.0.

*Primary Examiner* — Ibrahim Siddo
(74) *Attorney, Agent, or Firm* — IPUSA, PLLC

(57) ABSTRACT

A cassette connectable to a printer includes a housing configured to house a recording sheet, a connector that is connected to a feed port of the printer for supplying the recording sheet to the printer, and a sensor group including sensor modules that measure a state in a space surrounded by the housing.

6 Claims, 29 Drawing Sheets

(56) References Cited

U.S. PATENT DOCUMENTS

| | | | |
|---|---|---|---|
| 6,924,907 B1 | 8/2005 | Silverbrook et al. | |
| 6,956,669 B1 | 10/2005 | Silverbrook et al. | |
| 6,958,826 B1 | 10/2005 | Walmsley et al. | |
| 6,967,741 B1 | 11/2005 | Silverbrook et al. | |
| 6,975,429 B1 | 12/2005 | Walmsley et al. | |
| 7,259,889 B1 | 8/2007 | Walmsley | |
| 2010/0007074 A1* | 1/2010 | Iguchi .................... | B65H 29/34 270/58.08 |

FOREIGN PATENT DOCUMENTS

| | | |
|---|---|---|
| JP | S62-124942 U | 8/1987 |
| JP | 2003-500245 | 1/2003 |
| JP | 2004-059222 | 2/2004 |
| JP | 2009-291354 | 12/2009 |
| JP | 2010-52231 | 3/2010 |
| KR | 10-2018-0057825 | 5/2018 |

* cited by examiner

FIG.18

|  | | LIGHT RECEPTION | | | | | |
|---|---|---|---|---|---|---|---|
|  | | a1 | a2 | a3 | b1 | b2 | b3 |
| LIGHT EMIS- SION | a1 |  | 1 | 0 | 0 | 0 | 0 |
| | a2 | 0 |  | 0 | 0 | 0 | 0 |
| | a3 | 0 | 0 |  | 0 | 0 | 0 |
| | b1 | 0 | 0 | 0 |  | 0 | 0 |
| | b2 | 0 | 0 | 0 | 0 |  | 0 |
| | b3 | 0 | 0 | 0 | 0 | 0 |  |

CASSETTE AND SYSTEM

CROSS-REFERENCE TO RELATED APPLICATION

The present application is based on and claims priority to Japanese Patent Application No. 2018-115289, filed on Jun. 18, 2018, the entire contents of which are incorporated herein by reference.

BACKGROUND OF THE INVENTION

1. Field of the Invention

An aspect of this disclosure relates to a cassette and a system.

2. Description of the Related Art

Japanese Laid-Open Patent Publication No. 2003-500245 discloses a printer system including a printer module and an expansion module connectable to the printer module. Japanese Laid-Open Patent Publication No. 2009-291354 discloses a measuring device capable of measuring the abdominal circumference based on values output from sensors disposed inside of a frame.

With related-art technologies, the measuring device need to be connected to a printer via a cable or transmit data to the printer to print measurement results. Thus, it is bothersome to print measurement results.

SUMMARY OF THE INVENTION

In an aspect of this disclosure, there is provided a cassette connectable to a printer. The cassette includes a housing configured to house a recording sheet, a connector that is connected to a feed port of the printer for supplying the recording sheet to the printer, and a sensor group including sensor modules that measure a state in a space surrounded by the housing.

BRIEF DESCRIPTION OF THE DRAWINGS

FIG. 18 is a table for recording the results of receiving light by the sensor modules according to the first embodiment;

DESCRIPTION OF EMBODIMENTS

Embodiments of the present invention are described below with reference to the accompanying drawings.

Figure 1:
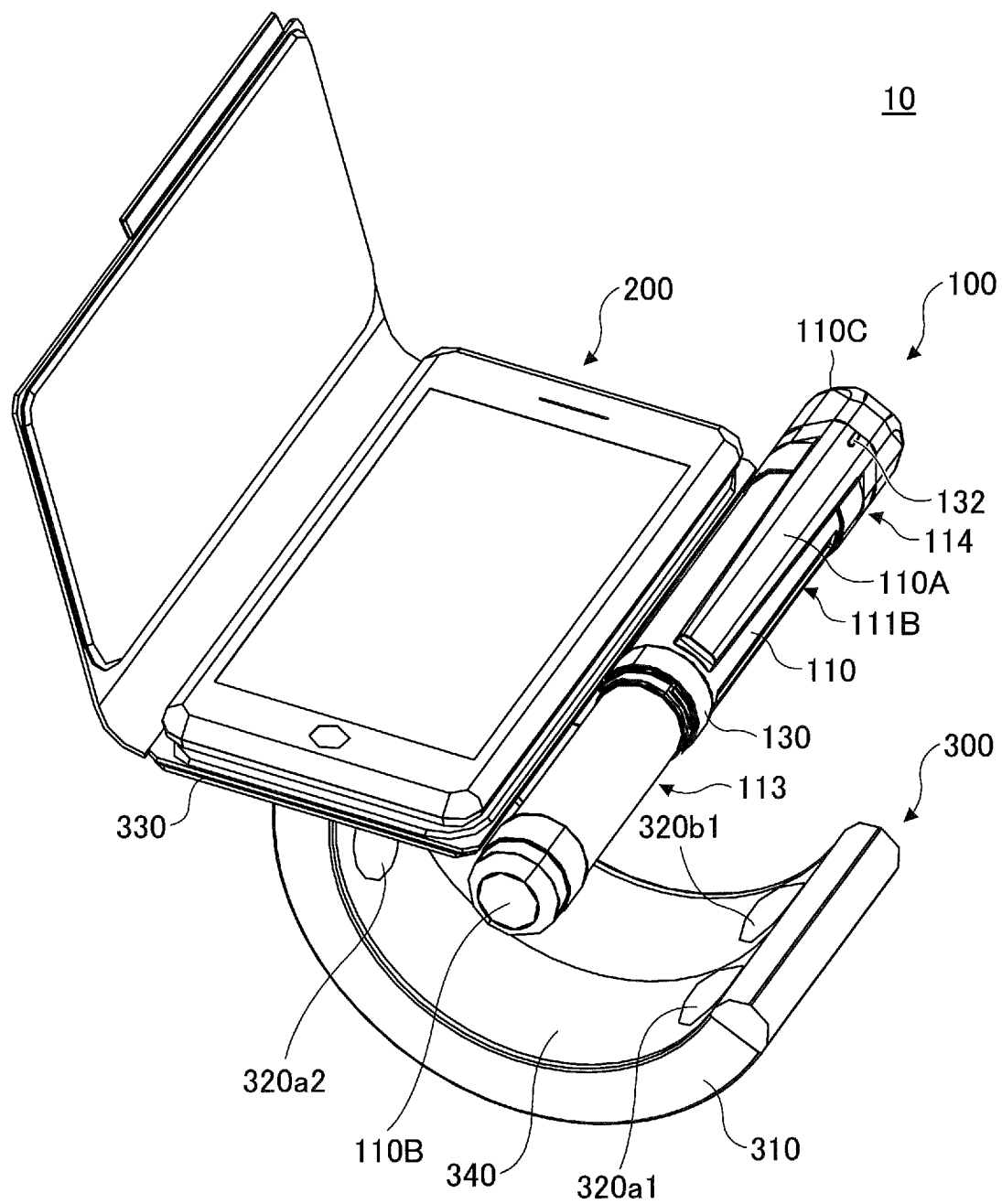
FIG. 1 is a perspective view of a system according to an embodiment.
Figure 2:
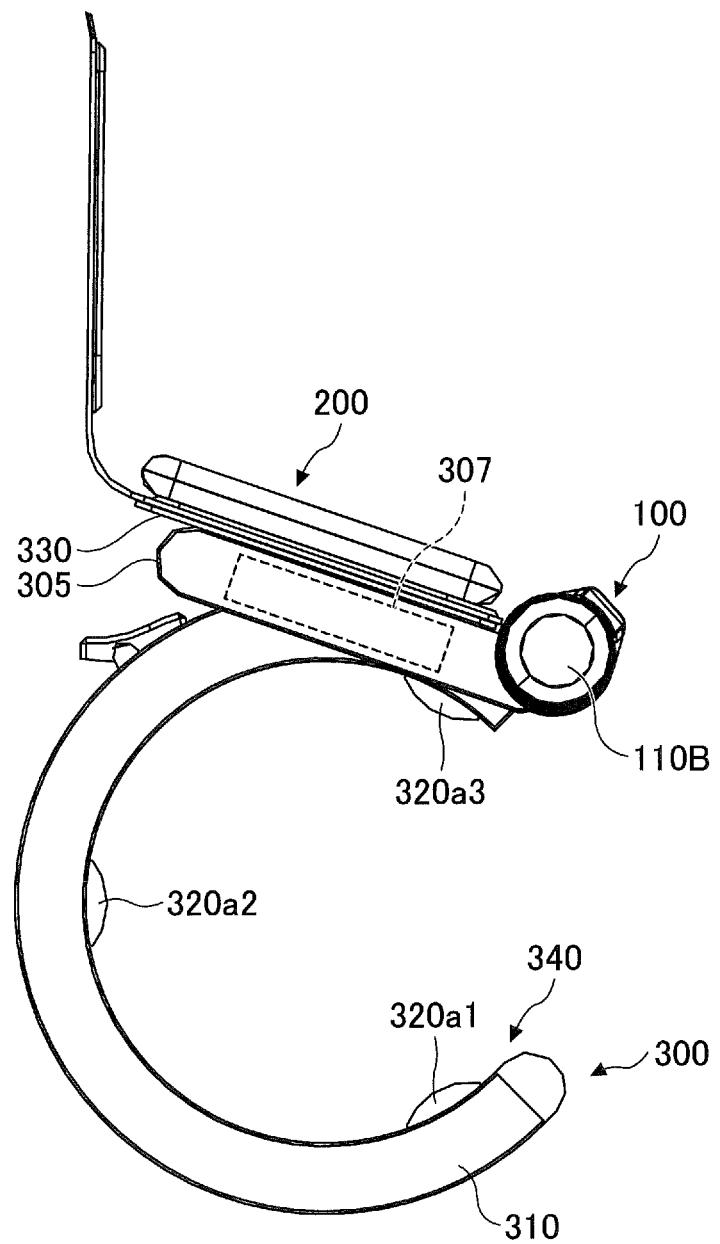
FIG. 2 is a side view of the system of FIG. 1.
Figure 3:
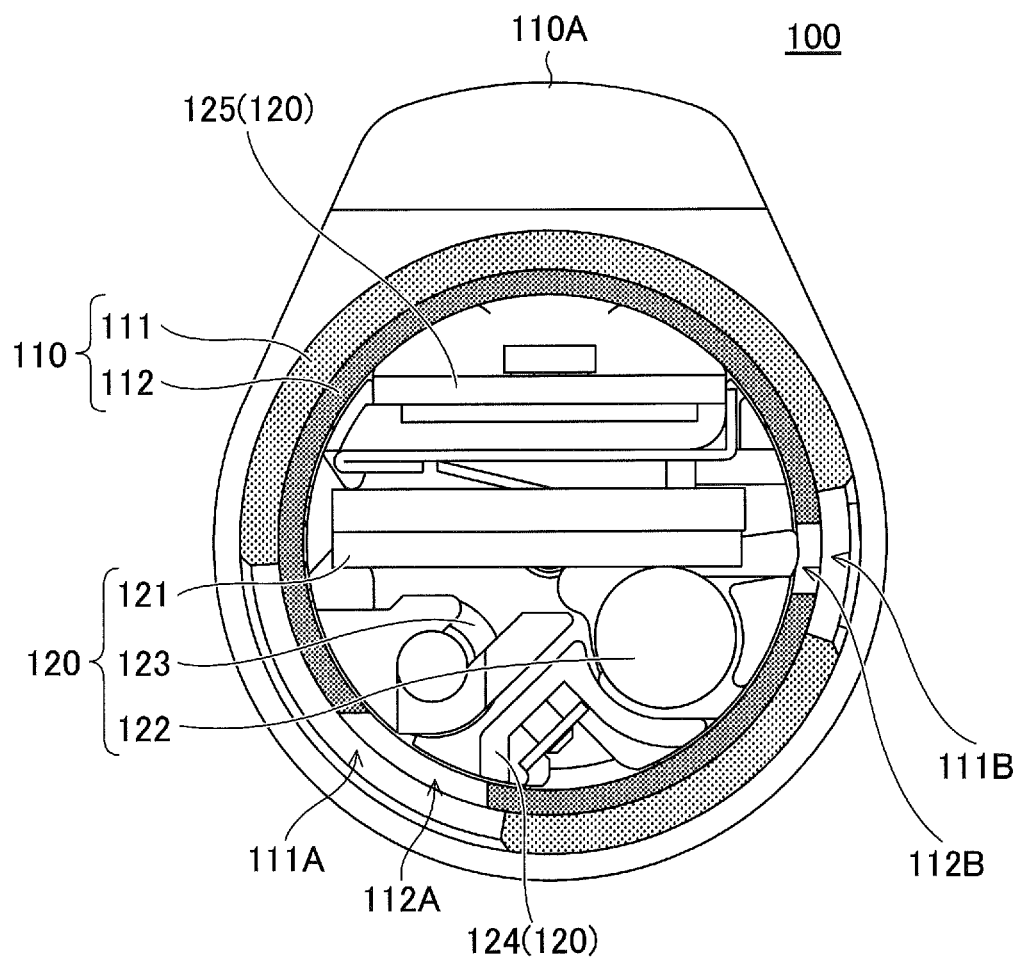
FIG. 3 is a cross-sectional view of a terminal according to an embodiment.

FIG. 1 is a perspective view and FIG. 2 is a side view of a system 10 according to an embodiment. FIG. 3 is a cross-sectional view of a terminal device 100 according to the embodiment. As illustrated, the system 10 includes the terminal 100, a smartphone 200, and a cassette 300.

The terminal 100 is a pen-shaped, portable IOT (Internet of Things) device. The terminal 100 may have a diameter of about 18 mm to 20 mm and a length of about 165 mm to 170 mm. The terminal 100 communicate via Bluetooth Low Energy (BLE) with the smartphone 200, which is an example of an "information terminal". The terminal 100 can share data with the smartphone 200 by communicating data between the smartphone 200.

The terminal 100 includes a housing 110 that can be divided into a power source 113 and a print module 114. The print module 114 is driven by power supplied from the power source 113. The print module 114 includes a printer 120 that prints information on paper (recording sheet) P supplied from the cassette 300 attached to a feed port 111A and discharges the paper P through a discharge port 111B. The print module 114 can also be driven by power supplied from the cassette 300 connected to the print module 114. The print module 114 can print data wirelessly transmitted from the smartphone 200 and data stored in its memory.

A hook 110A is provided on the print module 114 so that the terminal 100 can be clipped to a chest pocket like a pen. A dial switch 130 is provided around the print module 114. The user may turn on and off and change the operating modes of the terminal 100 by operating the switch 130. The switch 130 is operated by pushing and rotating. An indicator 132 indicates states of the terminal 100 such as a power on/off state, a printing state, and operation modes with light. A light emitting diode (LED) may be used as the indicator 132. A cap 110B is provided at one end of, and a cap 110C is provided at the other end of the housing 110.

The cassette 300 supplies paper P and power to the terminal 100. The cassette 300 includes an arc-shaped housing 310 that extends from a body 305 and houses the paper P. When a connector 380 is connected to the feed port 111A, the cassette 300 supplies the paper P housed in the housing 310 to the printer 120. The housing 310 is shaped like a clip and can be attached to, for example, a transparent pipe. Sensor modules 320a1 through 320a3 and 320b1 through 320b3 (collectively, "sensor modules 320") are provided on the inner surface of the housing 310. The sensor modules 320 measure an object in a space surrounded by the housing 310. When the housing 310 is attached to a transparent pipe, the sensor modules 320 can be used to determine whether an object exists in the pipe, and the shape, the size, the moving direction, and the moving speed of the object. The sensor modules 320 may be used to count the number of objects such as fish or foreign objects in a liquid or the number of objects such as balls passing through the pipe. In the present embodiment, two groups of sensor modules are disposed apart from each other in the lateral direction of the inner surface of the housing 310. Each sensor group includes three sensor modules 320 that are arranged at regular intervals. The cassette 300 includes a processor 307 such as an integrated circuit (IC) provided in the body 305. The processor 307 stores and internally processes data obtained from the sensor modules 320. The processor 307 can transmit the sensor data to the terminal 100 to print, externally process, store, or distribute the sensor data. The cassette 300 includes a table 330 disposed on the body 305 for mounting the smartphone 200.

The housing 110 includes an outer cylinder 111 and an inner cylinder 112 inserted into the outer cylinder 111. The outer cylinder 111 is rotatable relative to the inner cylinder 112. The feed port 111A and the discharge port 111B are formed in the outer cylinder 111. A feed port 112A and a discharge port 112B are formed in the inner cylinder 112.

The printer 120 including a thermal head 121, a platen roller 122, a feed roller 123, a guide 124, and a controller 125 is provided inside of the inner cylinder 112.

Heating elements arranged in the thermal head 121 are controlled by a signal from the controller 125 to form an image on the paper P. The platen roller 122 is disposed to face the thermal head 121.

The feed roller 123 rotates to convey the paper P fed through the feed port 111A and the feed port 112A, along the guide 124 to a gap between the thermal head 121 and the platen roller 122.

The controller 125 includes a head drive circuit and a motor drive circuit. The head drive circuit controls the thermal head 121 based on control data corresponding to print data. The motor drive circuit controls the operation of a pulse motor for feeding paper based on control data corresponding to printing timing.

Figure 4:
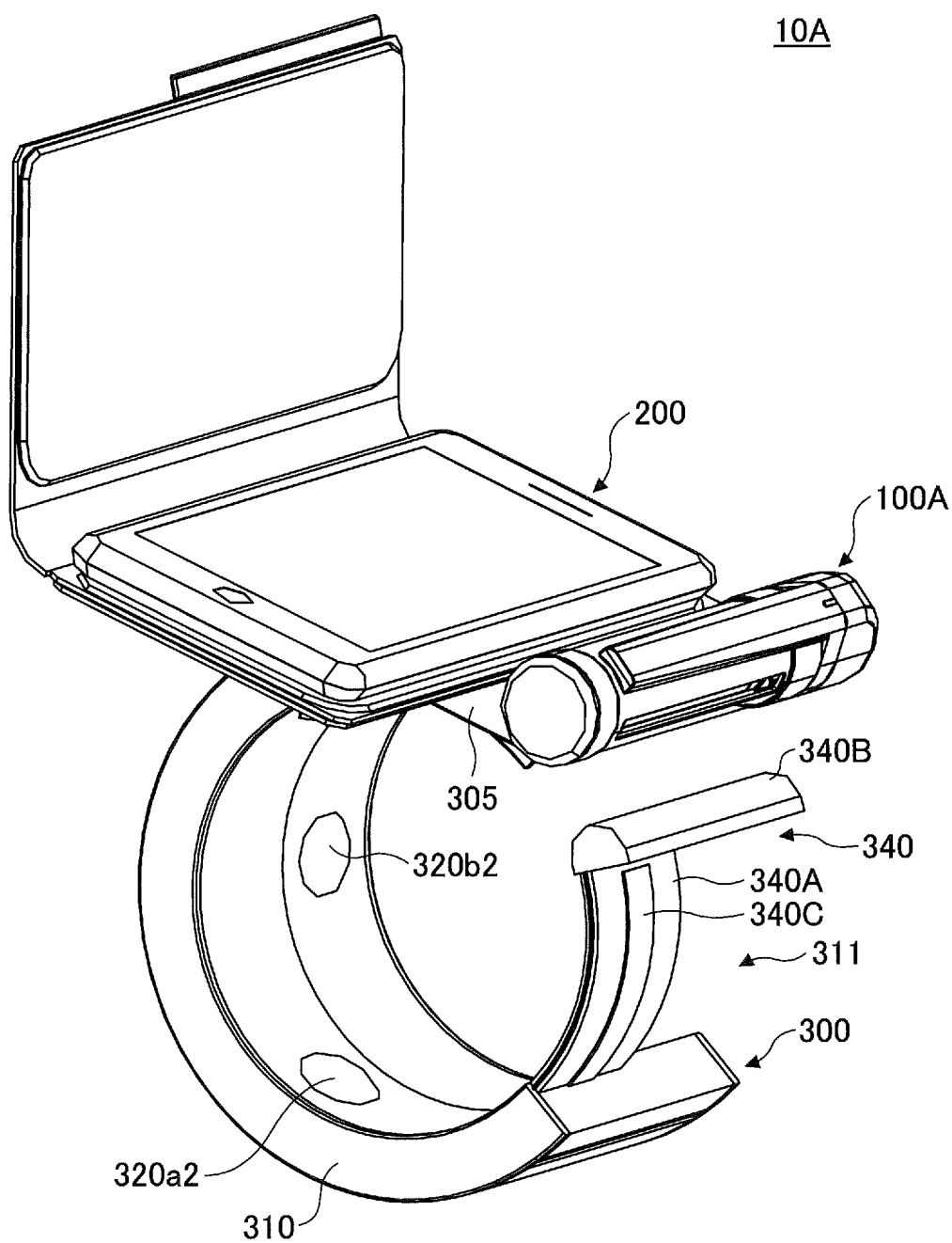
FIGS. 4 and 5 illustrate a system according to a variation of the embodiment and a structure for attaching an arm.
Figure 5:
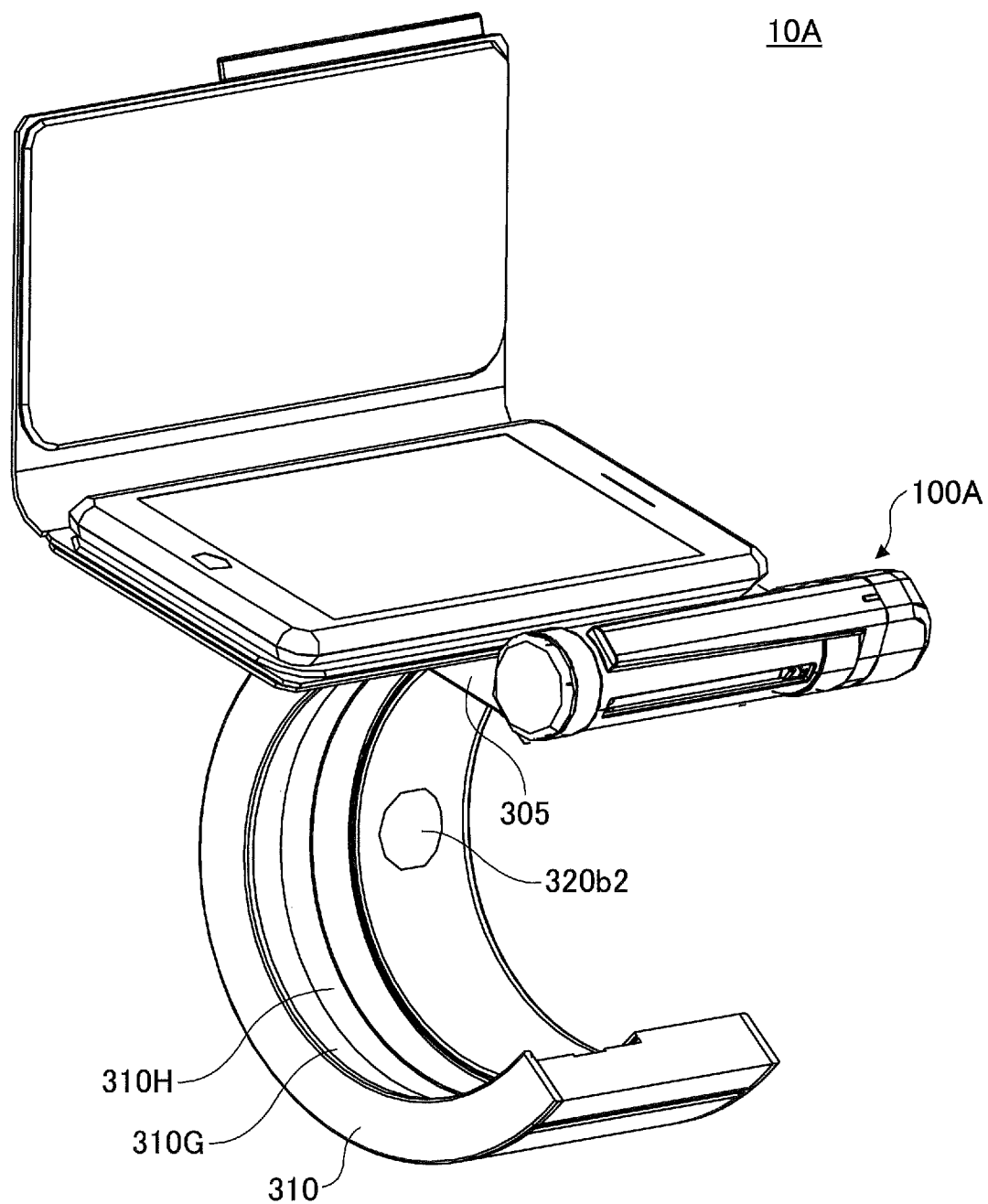

FIGS. 4 and 5 illustrate a system 10A that is a variation of the system 10. The system 10A includes a terminal 100A. The terminal 100A can be driven by a 2-cell lithium-ion battery provided in the cassette 300.

FIGS. 4 and 5 also illustrates a structure for attaching an arm 340. The housing 310 includes the arm 340 that forms a portion of the inner surface of the cassette 300 and is slidable in the circumferential direction. The arm 340 slides to protrude from the front end of the housing 310 and close an opening 311 between the front end and the rear end of the housing 310, to prevent an object such as a pipe from being detached from the housing 310. One of the two sensor groups is provided on the arm 340 and moves along with the sliding arm 340. As illustrated in FIG. 5, a groove 310G is formed along the circumferential direction in the inner surface of the housing 310. The side edges of the arm 340 are fitted into the side edges of the groove 310G so that the arm 340 can slide along the groove 310G. A groove 310H is formed in the middle of the groove 310G. The groove 310H engages with a rib 340C formed on the outer surface of the arm 340 to guide the sliding movement of the arm 340.

Figure 6:
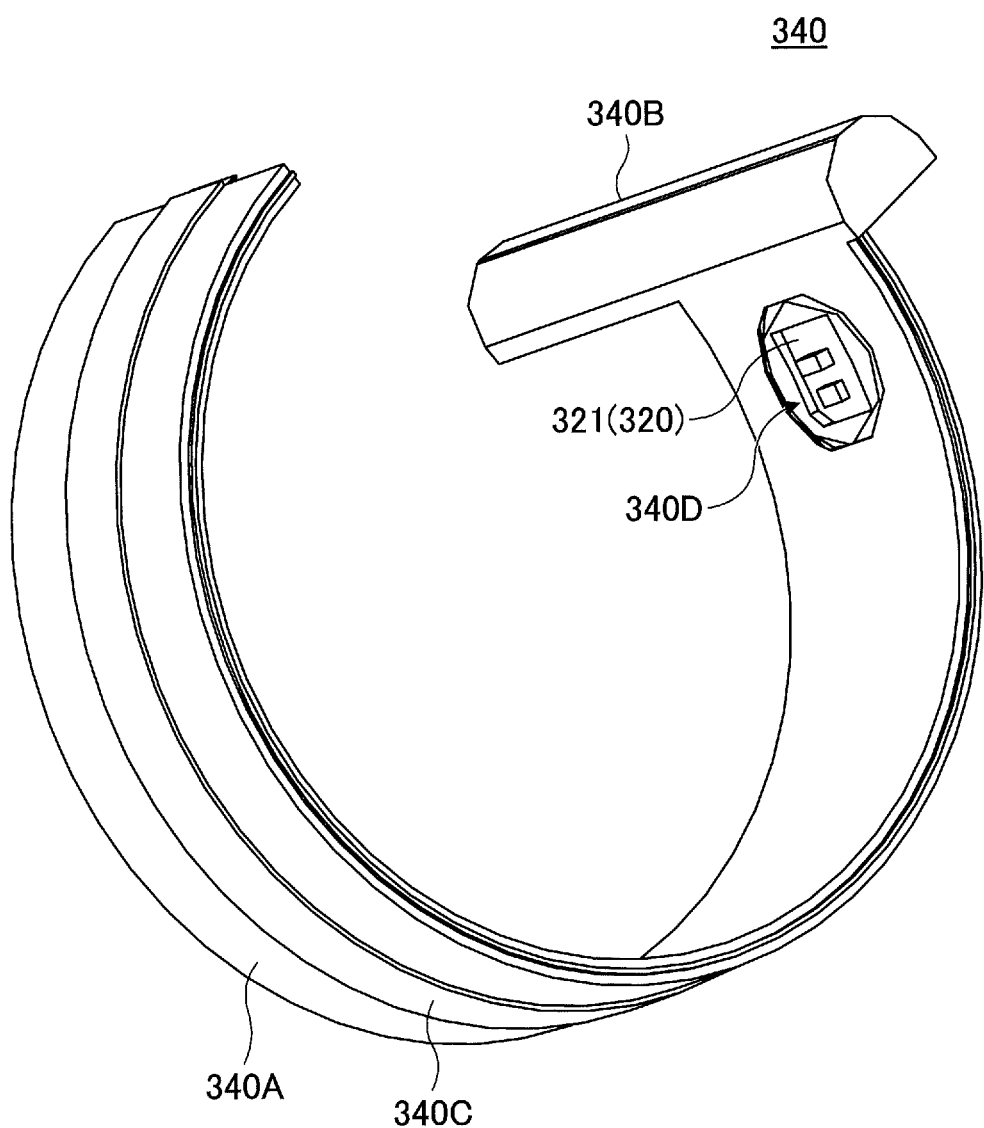
FIGS. 6 and 7 illustrate an arm.
Figure 7:
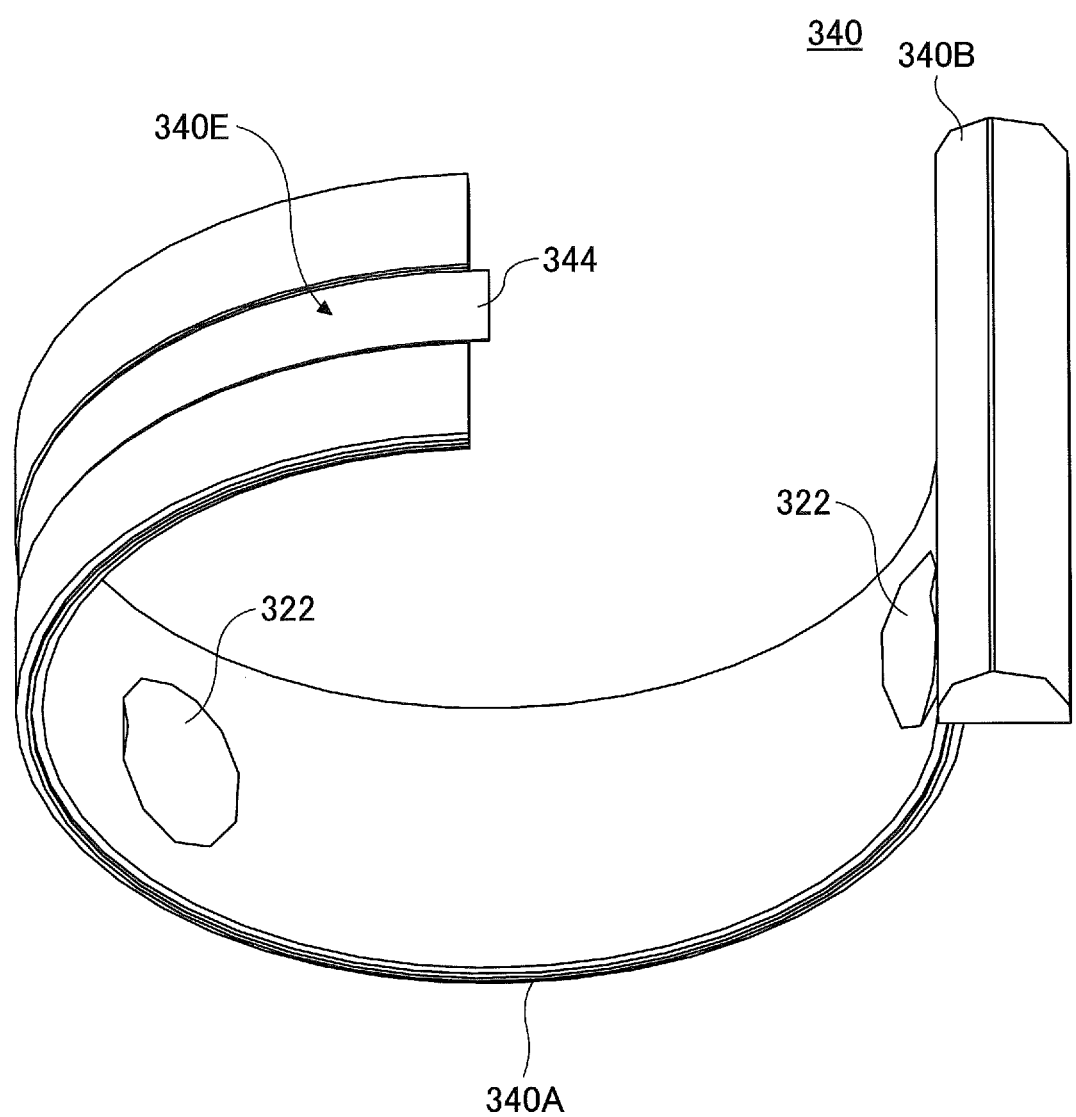

FIGS. 6 and 7 illustrate the arm 340. The arm 340 includes an arc-shaped arm part 340A and a grip 340B provided at the front end of arm part 340A. The grip 340B is held by the user when sliding the arm 340. The rib 340C is formed on the outer surface of the arm part 340A.

Openings 340D are formed in the inner surface of the arm part 340A. Each of the openings 340D has the same shape as a substrate 321 of the sensor module 320. The sensor modules 320 can be easily and securely placed by fitting the sensor modules 320 into the openings 340D. The opening 340D and the substrate 321 have a rectangular shape, and a corresponding corners of the opening 340D and the substrate 321 are chamfered to fit the substrate 321 into the opening 340D in a correct orientation, to prevent the sensor module 320 from being damaged by an incorrect connection. A cover 322 is placed over the opening 340D to protect the sensor module 320.

Figure 10:
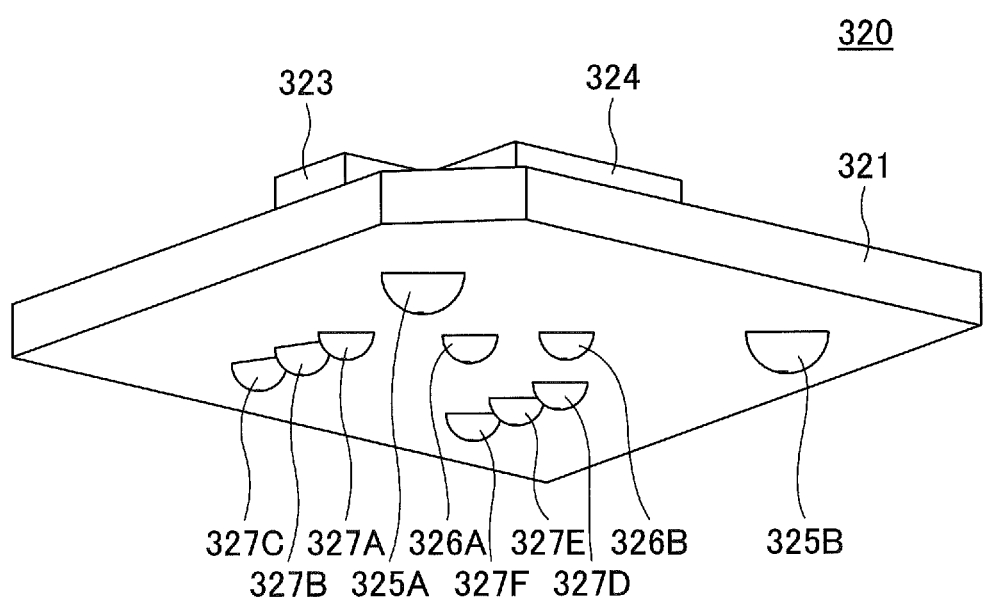
FIG. 10 illustrates a back surface of the sensor module.

The rib 340C formed in the outer surface of the arm part 340A is attachable to a groove 340E. FIG. 10 illustrates the exposed groove 340E as the rib 340c is detached. A flexible printed circuit (FPC) 344 is placed in the groove 340E, and is disposed between the groove 340E and the rib 340C when the rib 340C is attached to the arm part 340A. The FPC 344 is connected to the sensor modules 320, and transmits signals from the controller to the sensor modules 320.

Figure 8:
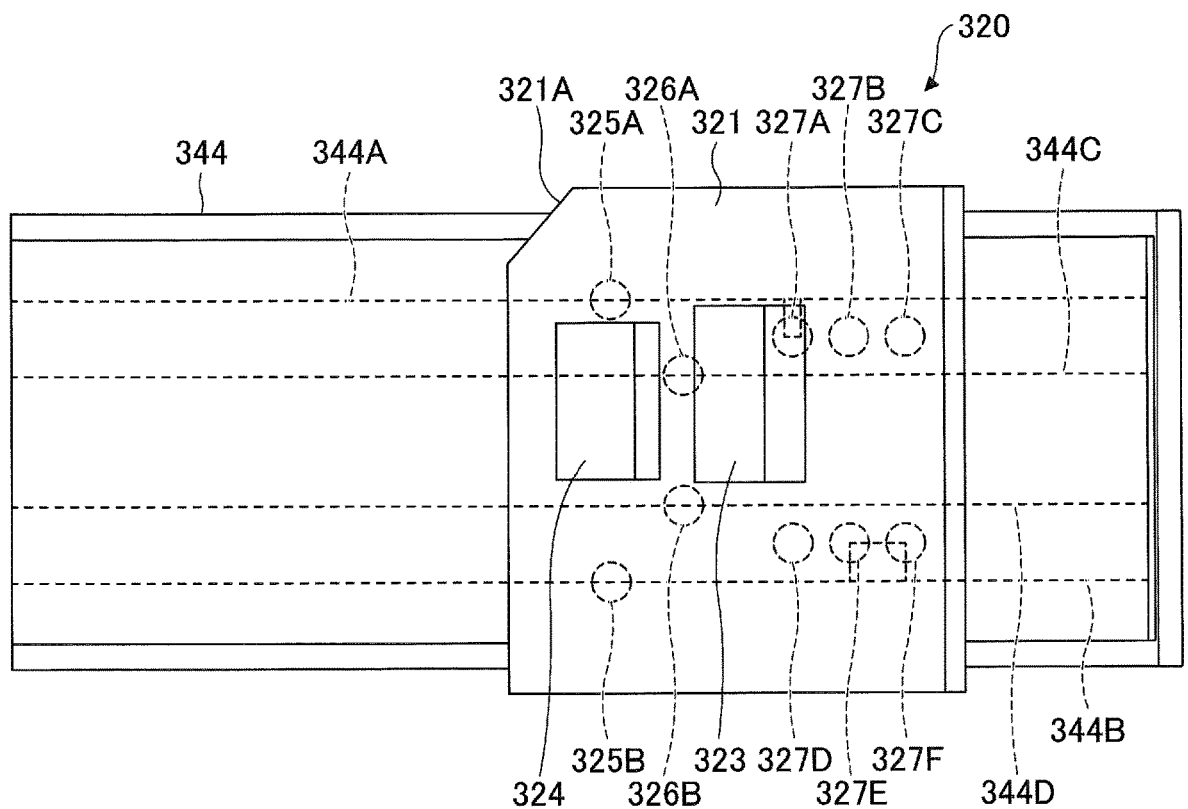
FIG. 8 is a plan view of an FPC and a sensor module.
Figure 9:
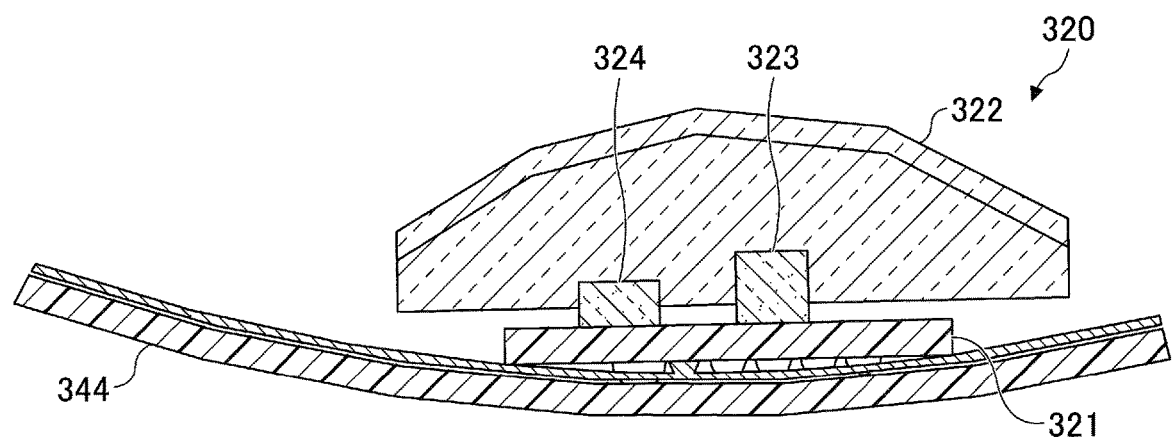
FIG. 9 is a cross-sectional view of the FPC and the sensor module.

FIG. 8 is a plan view, and FIG. 9 is a cross-sectional view of the FPC 344 and the sensor module 320. FIG. 10 illustrates a back surface of the sensor module 320.

A light emitter 323 and a light receiver 324 are provided on the substrate 321. Power supply terminals 325A and 325B and signal terminals 326A and 326B are provided on the back surface of the substrate 321. The light emitter and the light receiver are examples of sensors, and other types of sensors may be used.

The FPC 344 includes power supply wires 344A and 344B and signal wires 344C and 344D. The wires 344A and 344B supply power from the controller to the sensor module 320. The wires 344C and 344D receive a signal for controlling the light emitter 323 from the controller and transmit a signal from the light receiver 324 to the controller.

When the substrate 321 is fitted into the opening 340D, the terminals 325A and 325B are connected to the wires 344A and 344B, and the terminals 326A and 326B are connected to the wires 344C and 344D.

Position detection terminals 327A through 327F are provided on the back surface of the substrate 321. When the substrate 321 is fitted into the opening 340D, some of the terminals 327A-327F contact with the wires 344A and 344B indicated by dotted lines in FIG. 8 in response to the position of the sensor module 320. Because a power supply voltage is supplied to the terminals contacts with the wires 344A and 344B, the sensor module 320 can identify the opening 340D in which the sensor module 320 is placed by identifying the terminals to which the power supply voltage is supplied, and report the identified opening 340D to the cassette 300. In FIG. 8, the wire 344A is shaped to contact the terminal 327A, by increasing the width, attaching a land-like part, or bending the wire path inward. Similarly, the wire 344B is shaped to contact the terminals 327E and 327F. The terminal 327A contacts the wire 344A, and the terminals 327E and 327F contact the wire 344B. The shapes of the wires 344A and 344B are changed depending on the positions of the openings 340D. Accordingly, the position the sensor module 320 is attached can be determined based on a combination of the terminals 327A, 327B, and 327C contacting the wire 344A and a combination of the terminals 327D, 327E, and 327F contacting the wire 344B. The sensor module 320 stores a table where combinations of terminals and identifiers of openings are associated with each other. The sensor module 320 identifies an opening where the sensor module 320 is located based on the table and the terminals contacting the wires 344A and 344B, and reports the identified opening together with an ID and sensor type of the sensor module 320 to the cassette 300. In FIG. 8, the sensor module 320 identifies the opening where the sensor module 320 is located based on the combination of terminals 327A, 327E, and 327F contacts with the wires 344A and 344B. The cassette 300 determines correspondence between the sensor modules 320 and the openings based on the IDs, the sensor types, and the opening identifier reported by the sensor modules 320, and controls the sensor modules 320 in accordance with the openings where the sensor modules 320 are located and the sensor types.

Three openings are also formed and arranged in a manner similar to the openings 340D in a portion of the inner surface of the housing 310 other than the arm 340. An FPC similar to the FPC 344 is embedded in the housing 310 to face the back side of the three openings. Similarly to the sensor modules 320, the sensor modules can easily be installed and electrically connected to the housing 310 at the portion other than the arm 340.

The sensor module 320 may be configured to receive control signals for the light emitter 323 and transmit signals from the light receiver 324 via Bluetooth Low Energy (BLE) communication instead of via the wires 344C and 344D.

Figure 11:
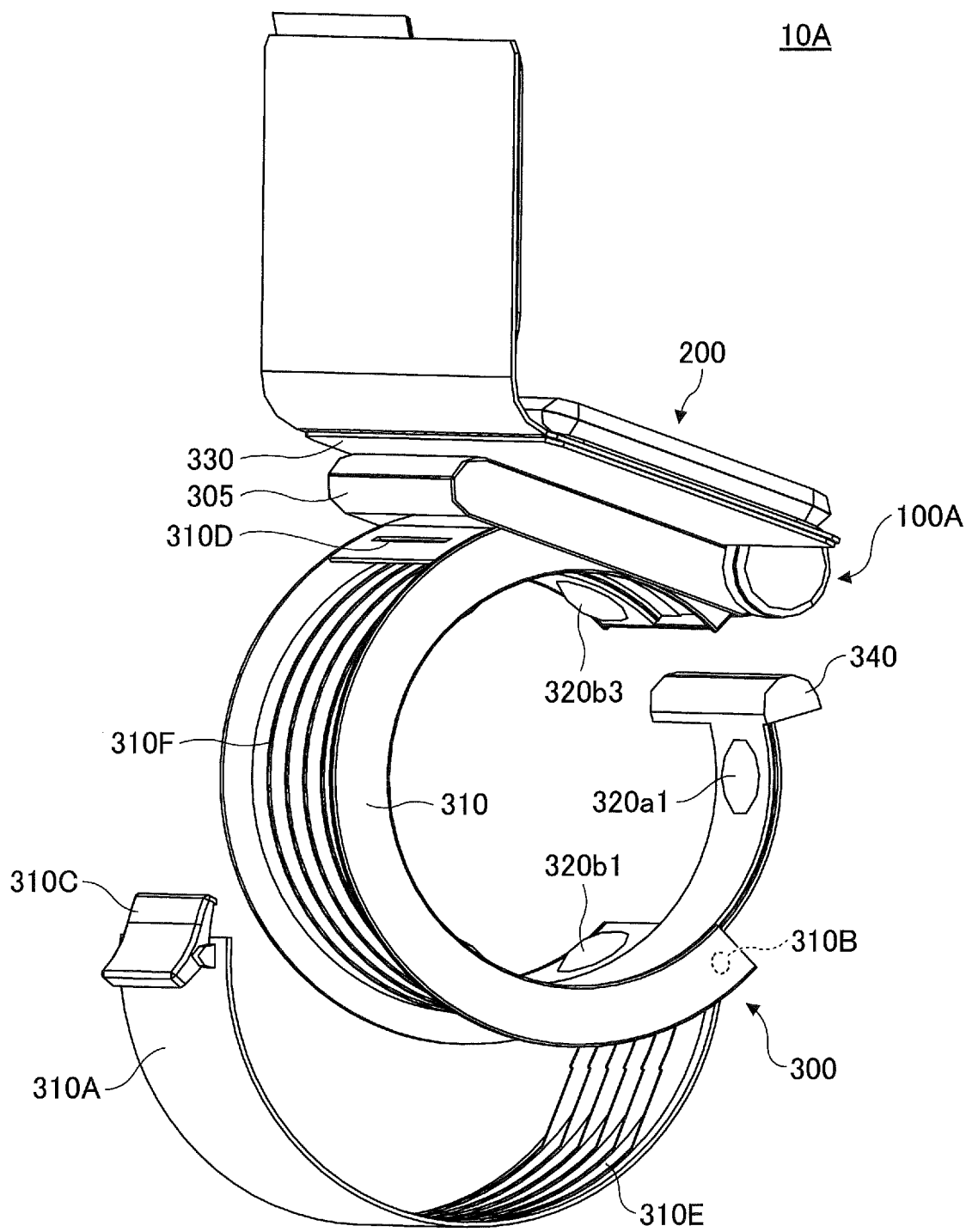
FIGS. 11 and 12 illustrate an outer wall of the housing.
Figure 12:
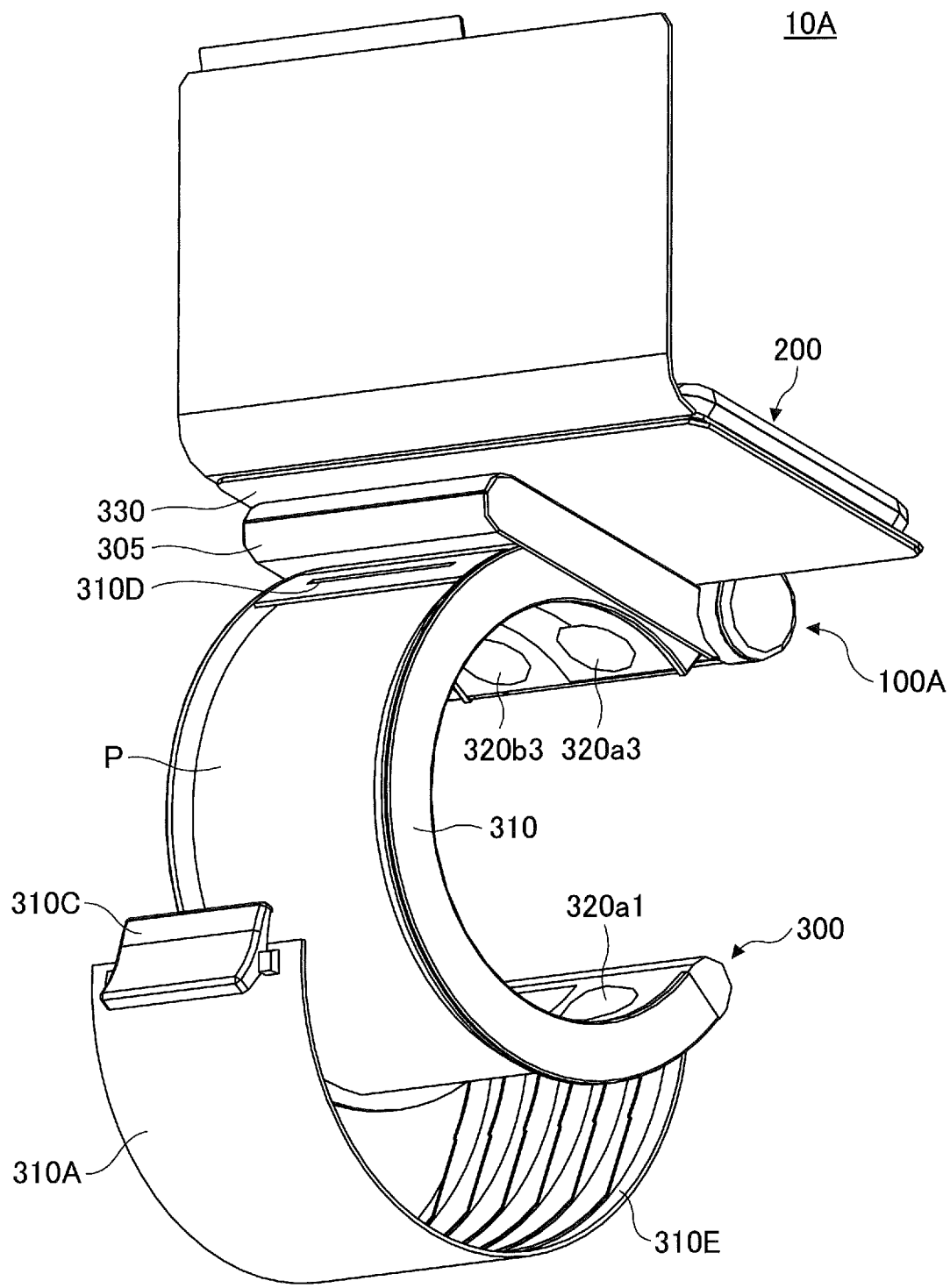

FIGS. 11 and 12 illustrates an openable and closable outer wall 310A of the housing 310. The housing 310 includes the wall 310A that is rotatably supported by a shaft 310B provided at the front end of the housing 310 to be opened and closed. The paper P can be installed in a space in the housing 310 by opening the wall 310A. For example, a label sheet with an A8 size (52×74 mm) may be used so that the terminal 100 can print a label that can be attached to a notebook. Because the wall 310A is opened in the radial direction, the paper P can be installed without sliding the arm 340. Because the sensor modules 320 need not be moved to install the paper P, it is not necessary to adjust the positions of the sensor modules 320 after installing the paper P. A hook 310C is provided at an end of the wall 310A. The wall 310A can be fixed in a closed position by engaging a claw at the end of the hook 310C with a groove 310D formed in the housing 310. Ribs 310E for guiding the paper P are formed on the inner surface of the wall 310A. Ribs 310F for guiding the paper P are formed on the inner surface of the housing 310.

Figure 13:
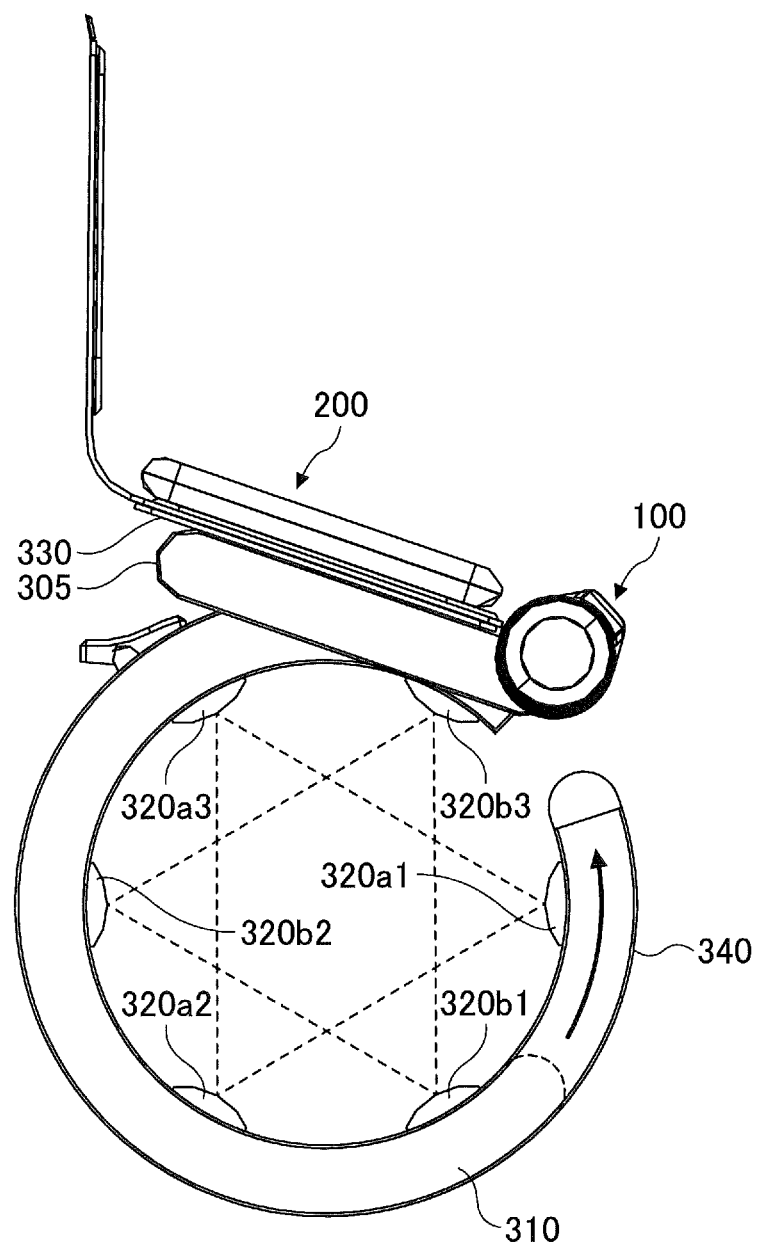
FIG. 13 illustrates positions on the housing where sensor modules are located.

FIG. 13 illustrates positions of the sensor modules 320 on the housing 310. The first sensor group and the second sensor group are disposed on the inner surface of the housing 310 and arranged apart from each other in a direction intersecting the circumferential direction. The first sensor group provided on the arm 340 includes three sensor modules 320a1, 320a2, and 320a3 that are arranged at a regular interval of 120 degrees in the circumferential direction. The second sensor group includes three sensor modules 320b1, 320b2, and 320b3 that are arranged at a regular interval of 120 degrees.

The sensor modules 320a1, 320a2, and 320a3 and the sensor modules 320b1, 320b2, and 320b3 are disposed in the same positions in the circumferential direction while the arm 340 is open. When the arm 340 is slid by 60 degrees, the positions of the sensor modules 320a1, 320a2, and 320a3 are shifted by 60 degrees from the sensor modules 320b1, 320b2, and 320b3 as illustrated in FIGS. 11 and 13.

Figure 14:
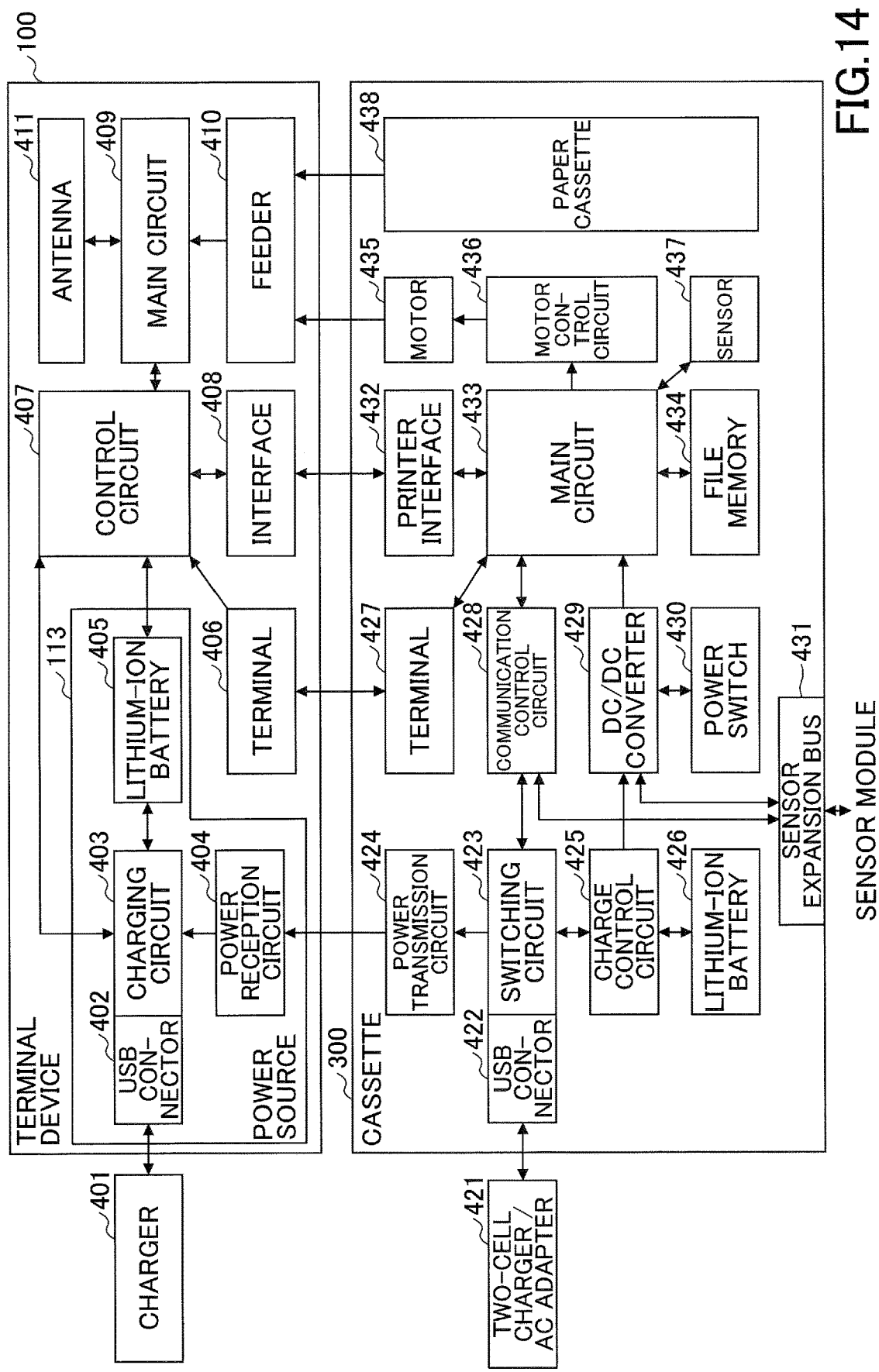
FIG. 14 illustrates a block diagram of a terminal and a cassette.

FIG. 14 illustrates a block diagram of the terminal 100 and the cassette 300. The power source 113 includes a USB connector 402, a charger 403, a receiver 404 for contactless charging, and a 1-cell lithium-ion battery 405. A charger 401 is connected to the USB connector 402 and supplies power to the charger 403. The receiver 404 contactlessly receives power from the cassette 300 and supplies the received power to the charger 403. The charger 403 charges the battery 405 with the power supplied from the charger 401 or the receiver 404. The battery 405 supplies power to components of the terminal 100.

The terminal 100 includes a power supply terminal 406, a control circuit 407 includes an operation controller/switching circuit/cassette interface (hereafter referred to as a "controller"), a communication interface 408, a main circuit 409 including BLE controller 409, a feeder 410, and an antenna 411. The terminal 406 receives power from the cassette 300 and supplies power to components of the terminal 100. The controller 407 controls process according to instructions via the switch 130. The controller 407 switches between an operation using the battery 405 as a power source, and an operation using a battery 426 as a power source. The controller 407 also controls communications with the cassette 300. The interface 408 is a terminal that physically and electrically connecting the cassette 300. The main circuit 409 controls operations of the terminal 100 and BLE communications. The feeder 410 feeds the paper P from the cassette 300 to a printing position. The antenna 411 transmits and receives radio waves in BLE communications.

The cassette 300 includes a USB connector 422, a switching circuit 423, a transmitter 424, a controller 425 that supports a 2-cell battery, a 2-cell lithium-ion battery 426, a power supply terminal 427, a communication controller 428, a DC/DC converter 429, a power switch 430, an expansion bus 431, a printer interface 432, a main circuit 433, a memory 434, a motor 435, a motor controller 436, a sensor 437, and a cassette 438.

A charger/AC adapter 421 ("charger") is connected to the USB connector 422 and supplies power to the switching circuit 423. The switching circuit 423 supplies power from the charger 421 to the transmitter 424, components of the cassette 300, or the controller 425. The transmitter 424 supplies power from the switching circuit 423 to the terminal 100 for contactless charging. The controller 425 charges the battery 426 using the power supplied from the switching circuit 423.

Power is supplied via the terminal 427 to the terminal 100. The controller 428 controls communications with the sensor modules 320 connected to the bus 431. The DC/DC converter 429 converts the voltage of power supplied to the cassette 300. The switch 430 turns on and off the cassette 300. The interface 432 controls communications with the terminal 100. The main circuit 433 controls operations of the cassette 300. The motor 435 drives the feeder 410 under the control of the motor controller 436.

Hardware components of the cassette 300 except for the cassette 438 are provided in the body 305.

Figure 15:
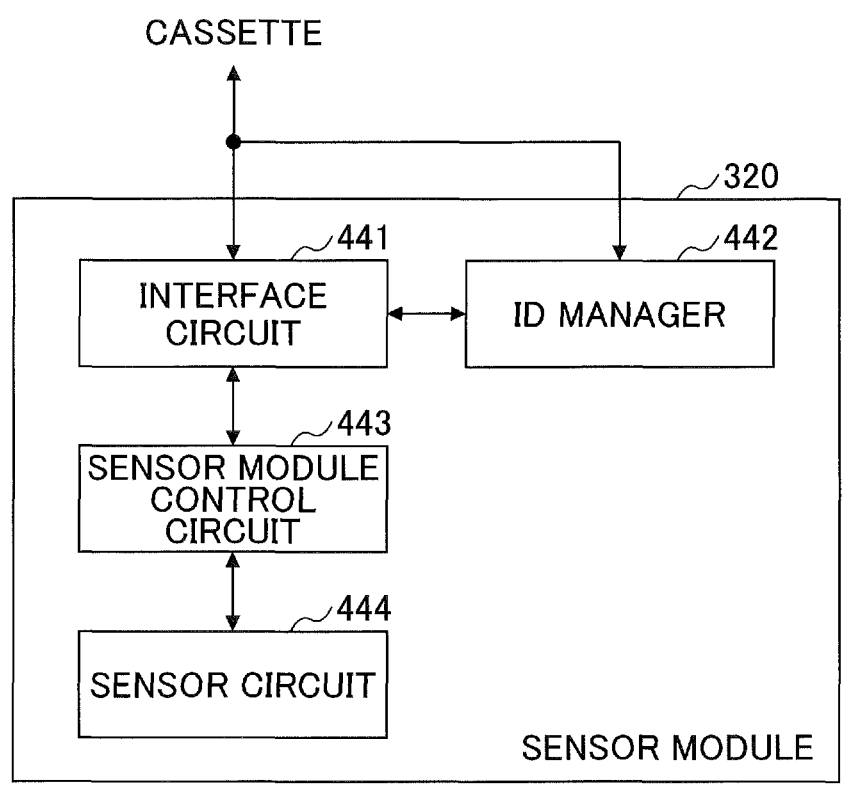
FIG. 15 illustrates a block diagram of a sensor module.

FIG. 15 illustrates a hardware configuration of the sensor module 320. The sensor module 320 includes an interface circuit 441, an ID manager 442, a sensor controller 443, and a sensor circuit 444. The interface circuit 441 controls communications with the cassette 300. The ID manager 442 manages the ID of the sensor module 320, and also manages information indicating the location of the sensor module 320 based on the connection states of the terminals 327A through 327F. Further, the ID manager 442 stores information indicating the type of a sensor in the sensor module 320. In response to a request from the cassette 300, the sensor module 320 transmits the ID, the location, and the sensor type to the cassette 300. The cassette 300 can identify the IDs, the locations, and the types of the sensors attached to the cassette 300. The controller 443 controls operations of the sensor module 320. The sensor circuit 444 controls the light emitter 323 and the light receiver 324.

Figure 16:
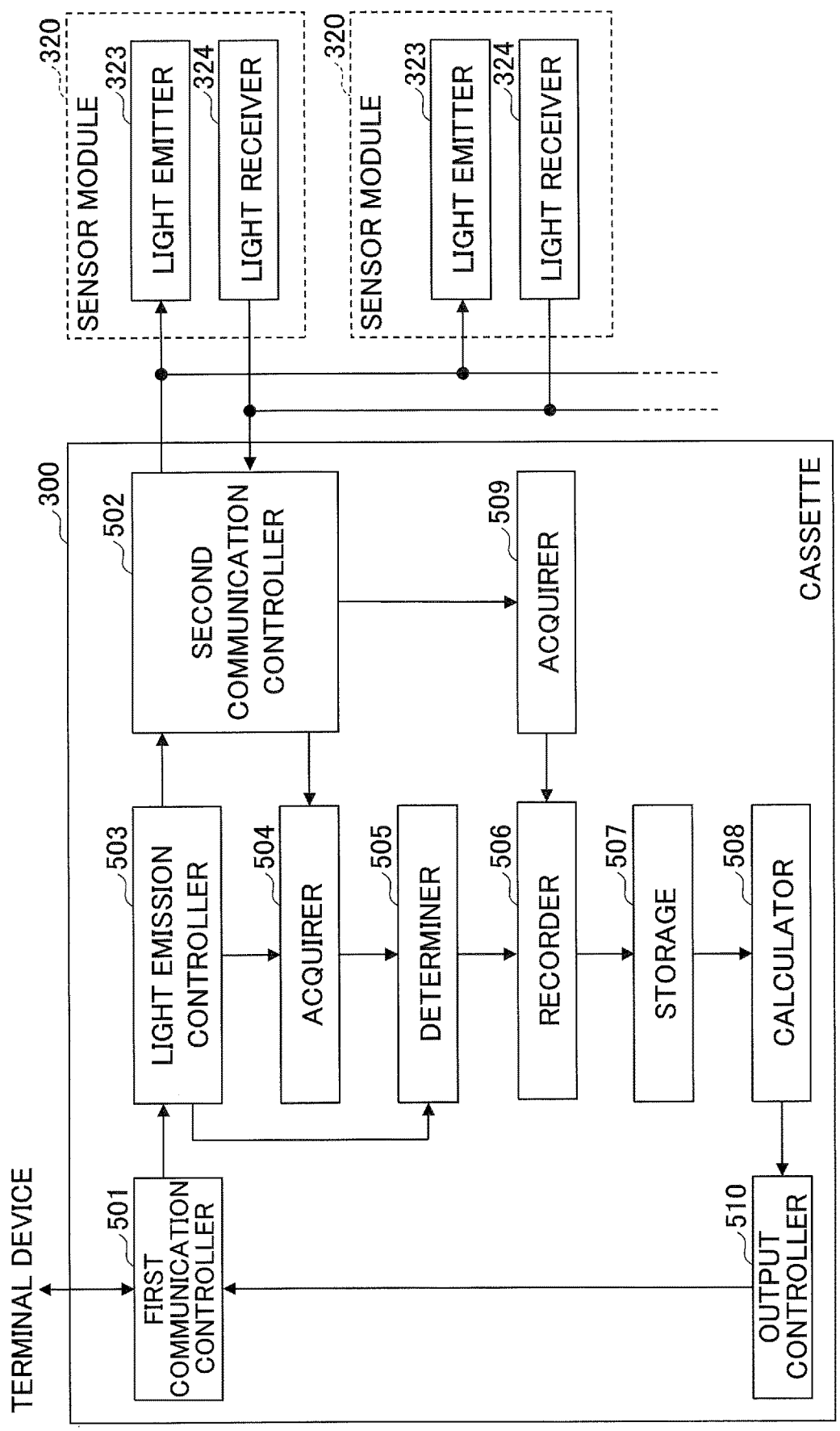
FIG. 16 illustrates a functional block diagram of a cassette.

FIG. 16 illustrates a functional configuration of the cassette 300. As illustrated in FIG. 16, the cassette 300 includes a first controller 501, a second controller 502, an emission controller 503, an acquirer 504, a determiner 505, a recorder 506, a storage 507, a calculator 508, an acquirer 509, and an output controller 510.

The first controller 501 controls communication connection and data communication with the terminal 100. The second controller 502 controls communication connection and data communication with the sensor modules 320.

The controller 503 controls the light emission of the light emitters 323 via the second controller 502. For example, the controller 503 sequentially emits the light emitters 323.

The acquirer 504 obtains detection values from the light receivers 324 via the second controller 502. Each time when the light emitter 323 of one of the sensor modules 320 emits light, the acquirer 504 obtains detection values from the light receivers 324 of the other sensor modules 320.

Based on the values obtained by the acquirer 504, the determiner 505 determines whether an object exists in a space surrounded by the housing 310. Each time any sensor module 320 emits light, the determiner 505 determines whether an object exists between the sensor modules 320 based on signal from the other sensor modules 320. The determiner 505 determines that, an object does not exist when the detection values are greater than or equal to a threshold, and an object exists when the detection values are less than the threshold.

For each combination of the sensor modules 320, the recorder 506 records the determination result of the determiner 505 in a table in the storage 507. The table stores correspondence between a combination of a light-emitted sensor module and a light-received sensor module, and the presence of an object. For example, the recorder 506 sets "1" indicating the presence of an object in a cell corresponding to a combination of sensor modules 320 received light, and sets "0" indicating the absence of an object in a cell corresponding to a combination of sensor modules 320 that has not received light. Also, an intermediate value may be set as a fuzzy value. The recorder 506 also records sensor information the acquirer 509 obtained from each sensor module 320 in the storage 507.

The storage 507 stores a table indicating determination results of the determiner 505, and sensor information of the sensor modules 320.

The calculator 508 performs calculations based on the stored determination results. For example, the calculator 508 calculates the approximate shape and size of an object based on the determination results indicating whether the object exists between the respective sensor modules 320. If the recorder 506 stores information indicating time when the presence or the absence of the object between the sensor modules 320 is detected, the calculator 508 calculates the direction and speed of movement of the object based on the positions and the time at which the object is detected.

The acquirer 509 obtains sensor information from each sensor module 320 via the second controller 502. The acquirer 509 obtains an ID, installation location information, and sensor type from each sensor module 320.

The controller 510 transmits the calculation result of the calculator 508 to the terminal 100 via the first controller 501.

First Embodiment

Figure 17A:
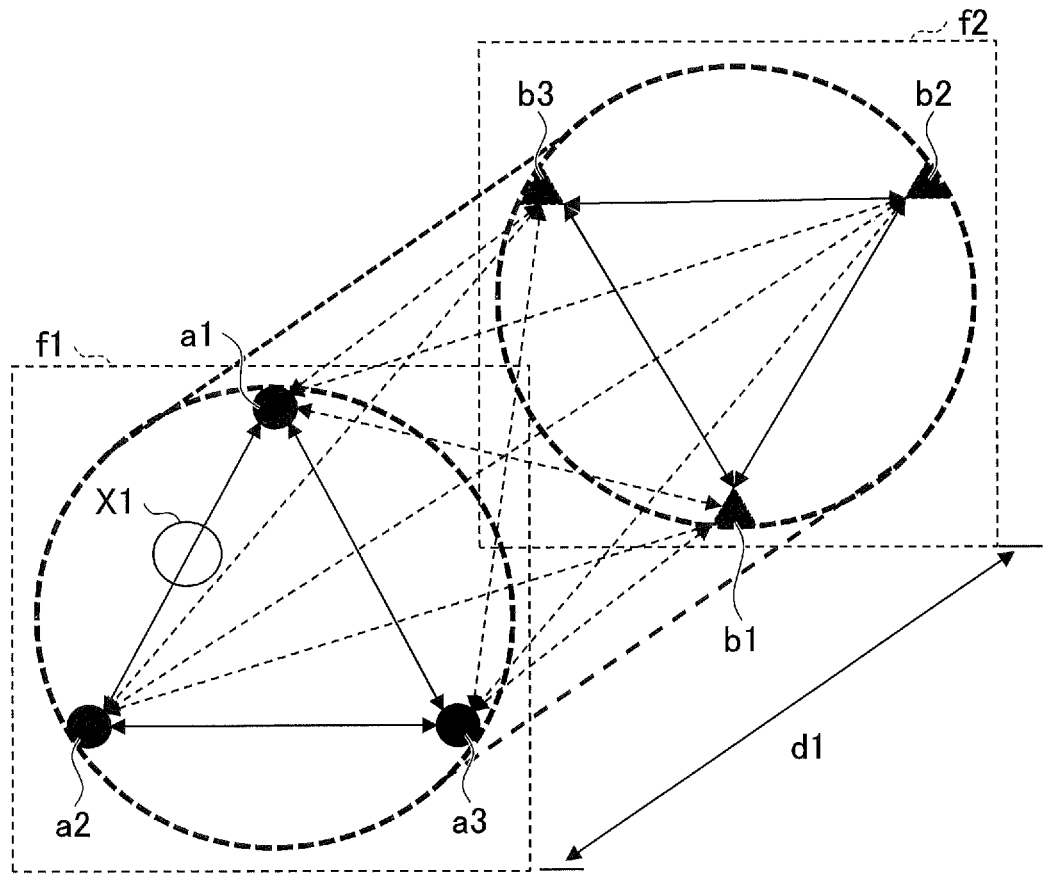
FIGS. 17A and 17B illustrates positions of sensor modules according to a first embodiment.
Figure 17B:
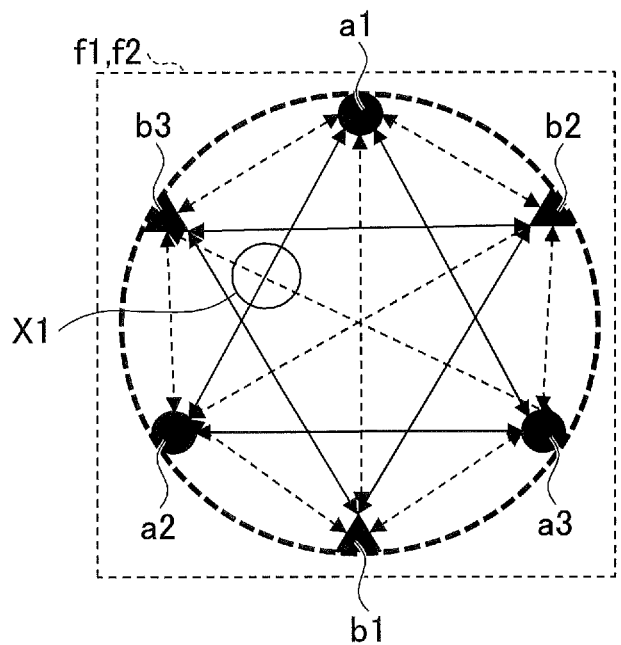

A method of detecting an object with the sensor modules 320 is described with reference to FIGS. 17A through 18. FIG. 17A illustrates positions of the sensor modules 320. FIG. 17B is an elevational view illustrating positions of the sensor modules 320. In FIGS. 17A and 17B, the positions of the sensor modules 320a1, 320a2, and 320a3 of the first sensor group disposed on a first virtual plane f1 are indicated by circles, and the positions of the sensor modules 320b1, 320b2, and 320b3 of the second sensor group disposed on a second virtual plane f2 are indicated by triangles. The first plane f1 and the second plane f2 are orthogonal to the inner surface of the housing 310. The first plane f1 and the second plane f2 are apart from each other by a distance dl.

Each sensor module 320 includes the light emitter 323 and the light receiver 324. Accordingly, each sensor module 320 can emit light, and receive light from another sensor module 320.

When a sensor module 320 receives light from another sensor module 320, the cassette 300 determines that there is no object between these sensor modules 320. When a sensor module 320 does not receive light from another sensor module 320, the cassette 300 determines that an object exists between these sensor modules 320.

The cassette 300 can determine whether an object exists in a space surrounded by the housing 310 by causing one of the sensor modules 320 to emit light at a time and determining whether the light is received by the other sensor modules 320.

As indicated by solid arrows in FIGS. 17A and 17B, the cassette 300 determines whether an object exists on the first plane f1 by emitting one of the sensor modules 320 on the first plane f1 and determining whether the other sensor modules 320 on the first plane f1 received the light.

Similarly, as indicated by solid arrows, the cassette 300 determines whether an object exists on the second plane f2 by emitting one of the sensor modules 320 on the second plane f2 and determining whether the other sensor modules 320 on the second plane f2 received the light.

Further, as indicated by dotted arrows, the cassette 300 determines whether an object exists between the first plane f1 and the second plane f2 by emitting one of the sensor modules 320 on the first plane f1 and determining whether the light is received by the sensor modules 320 on the second plane f2.

Similarly, as indicated by dotted arrows, the cassette 300 determines whether an object exists between the first plane f1 and the second plane f2 by emitting one of the sensor modules 320 on the second plane f2 and determining whether the light is received by the sensor modules 320 on the first plane f1.

FIG. 18 is a table for recording the results of receiving light by the sensor modules 320. The cassette 300 stores a table of FIG. 18 in a memory. The cassette 300 sets "1" in the cells of the table that correspond to combinations of light-emitted sensor modules and sensor modules that have not received light. For example, when the sensor module 320a1 has emitted light but the sensor module 320a2 has not received the light, the cassette 300 sets "1" in the cell corresponding to "light emission: a1" and "light reception: a2". Also, the cassette 300 sets "0" in the cells correspond to combinations of light-emitted sensor modules and sensor modules that have received light.

Figure 19:
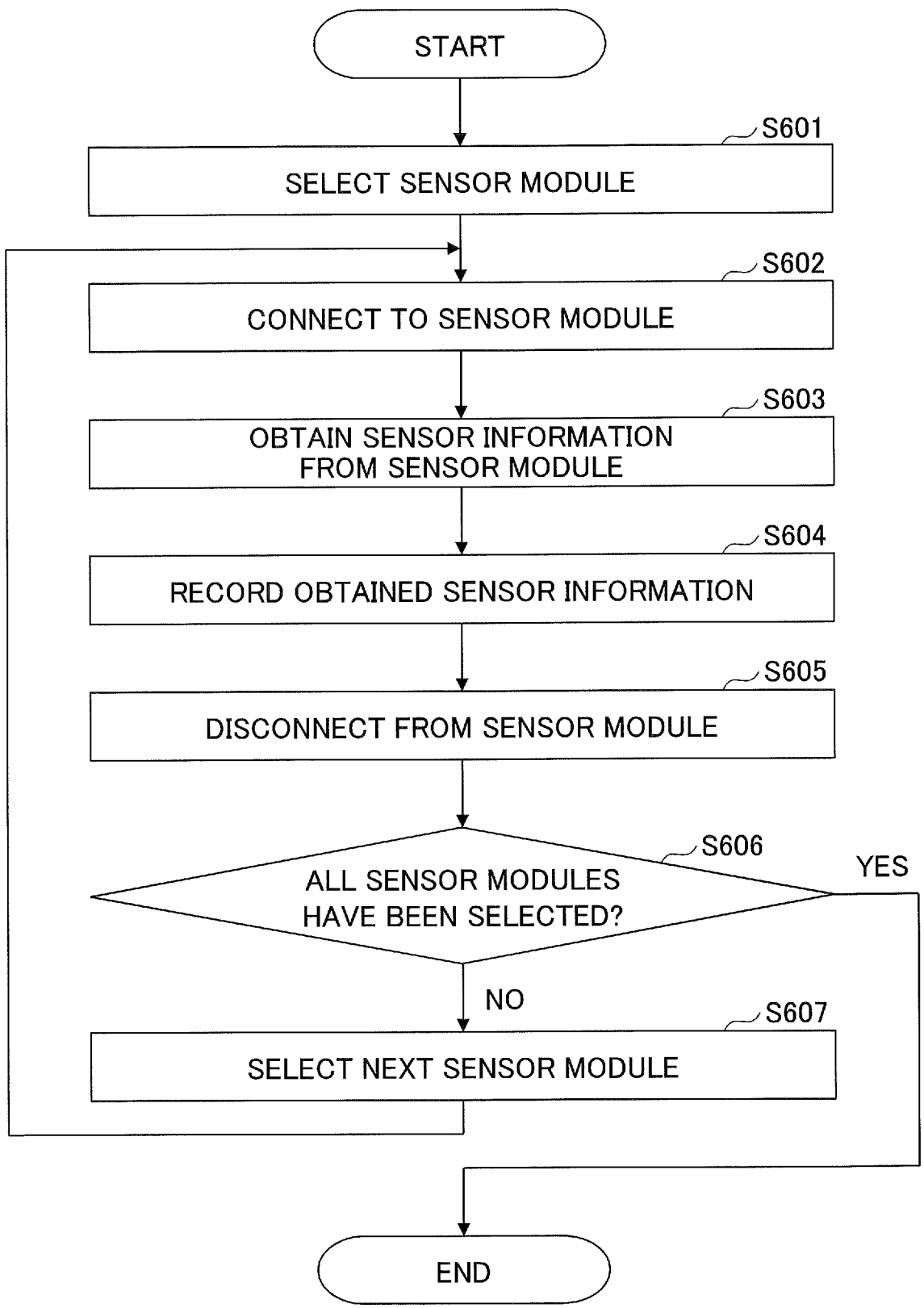
FIG. 19 is a flowchart illustrating an initial process according to the first embodiment.

FIG. 19 is a flowchart illustrating an initial process performed by the cassette 300. The process of FIG. 19 is started, for example, when the cassette 300 is turned on.

The second controller 502 selects one of the sensor modules 320 (S601), and connects to the selected sensor module 320 (S602). Next, the acquirer 509 obtains sensor information from selected sensor module 320 (S603), and the recorder 506 records the obtained sensor information in the storage 507 (S604). Then, the second controller 502 is disconnected from the sensor module 320 (S605).

Next, the second controller 502 determines whether all the sensor modules 320 have been selected (S606). If not all of the sensor modules 320 have been selected (S606: NO), the second controller 502 selects the next sensor module 320 (S607), and the cassette 300 returns to S602. When all of the sensor modules 320 have been selected (S606: YES), the cassette 300 ends the process of FIG. 19.

Figure 20:
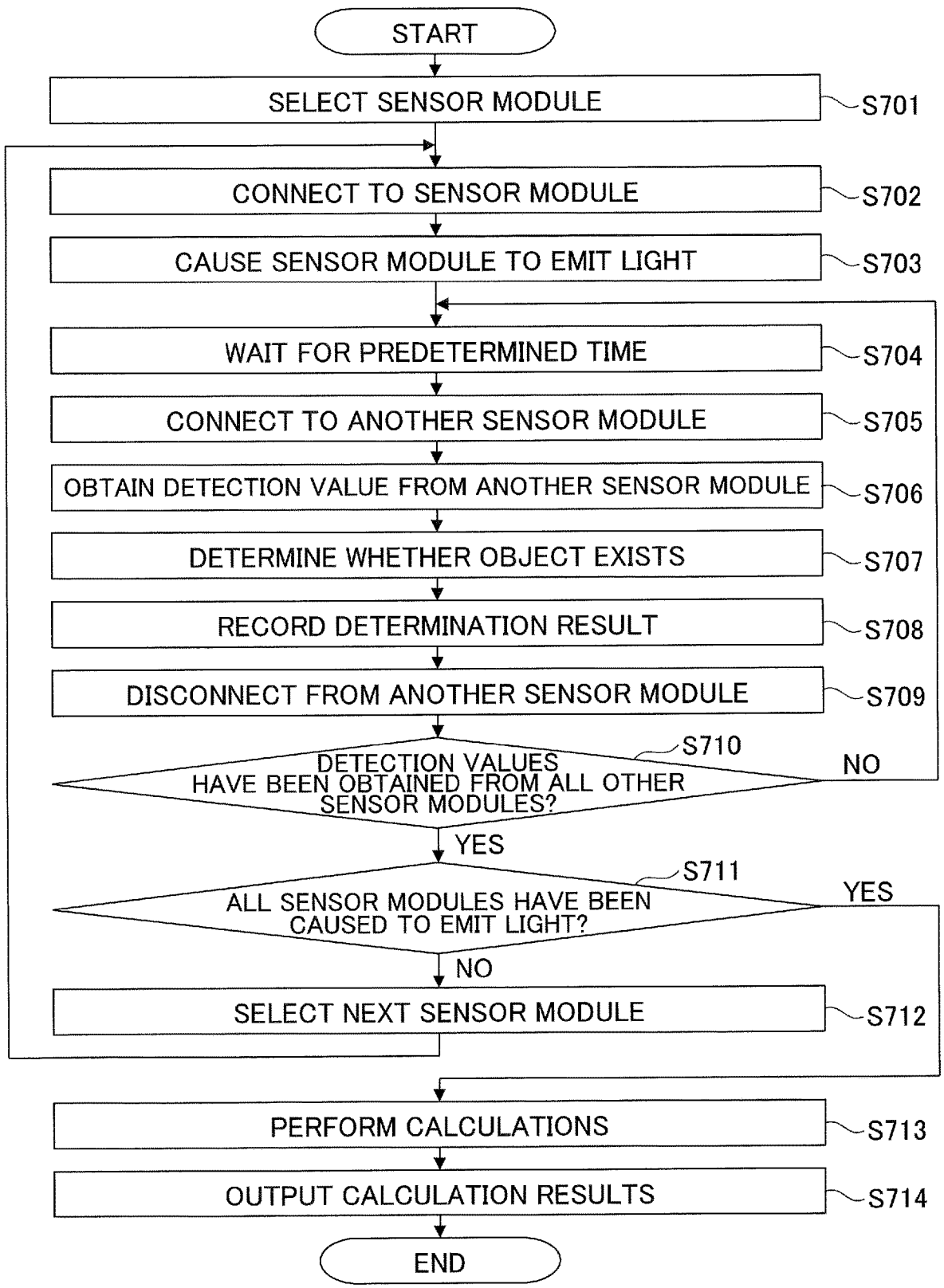
FIG. 20 is a flowchart illustrating a position detection process according to the first embodiment.

FIG. 20 is a flowchart illustrating a detection process performed by the cassette 300. The process of FIG. 20 is started, for example, when an instruction to execute the position detection is received from the terminal 100.

The second controller 502 selects one of the sensor modules 320 (S701) and connects to the selected sensor module 320 (S702). Then, the controller 503 causes the light emitter 323 of the selected sensor module 320 to emit light (S703).

Next, the second controller 502 waits for a predetermined time (S704), and then connects to another sensor module 320 (S705). Next, the acquirer 504 obtains a detection value of the light receiver 324 of the selected sensor module 320 (S706), the determiner 505 determines whether an object exists based on the obtained detection value (S707), and the recorder 506 records the determination result in the storage 507 (S708). Then, the second controller 502 is disconnected from the sensor module 320 (S709).

Next, the acquirer 504 determines whether detection values have been obtained from all other sensor modules 320 (S710). If detection values have not been obtained from all sensor modules 320 (S710: NO), the cassette 300 returns to S704.

When detection values have been obtained from all other sensor modules 320 (S710: YES), the controller 503 determines whether all of the sensor modules 320 have emitted light (S711). If not all of the sensor modules 320 have emit light (S711: NO), the second controller 502 selects the next sensor module 320 from the remaining sensor modules 320 (S712), and the cassette 300 returns to S702.

When all sensor modules 320 have emit light (S711: YES), the calculator 508 performs calculations based on the determination results stored in the storage 507 (S713), and outputs the calculation results to the terminal 100 (S714). The cassette 300 then ends the process of FIG. 20.

Thus, in the first embodiment, whether an object exists between sensor modules 320 can be determined based on the light reception states of two sensor modules 320. In the first embodiment, it is possible to determine whether an object exists between certain two sensor modules 320 located on the first plane f1, on the second plane f2, and on the first plane f1 and the second plane f2. Thus, the first embodiment can closely examine whether an object exists in the space.

Second Embodiment

Figure 21:
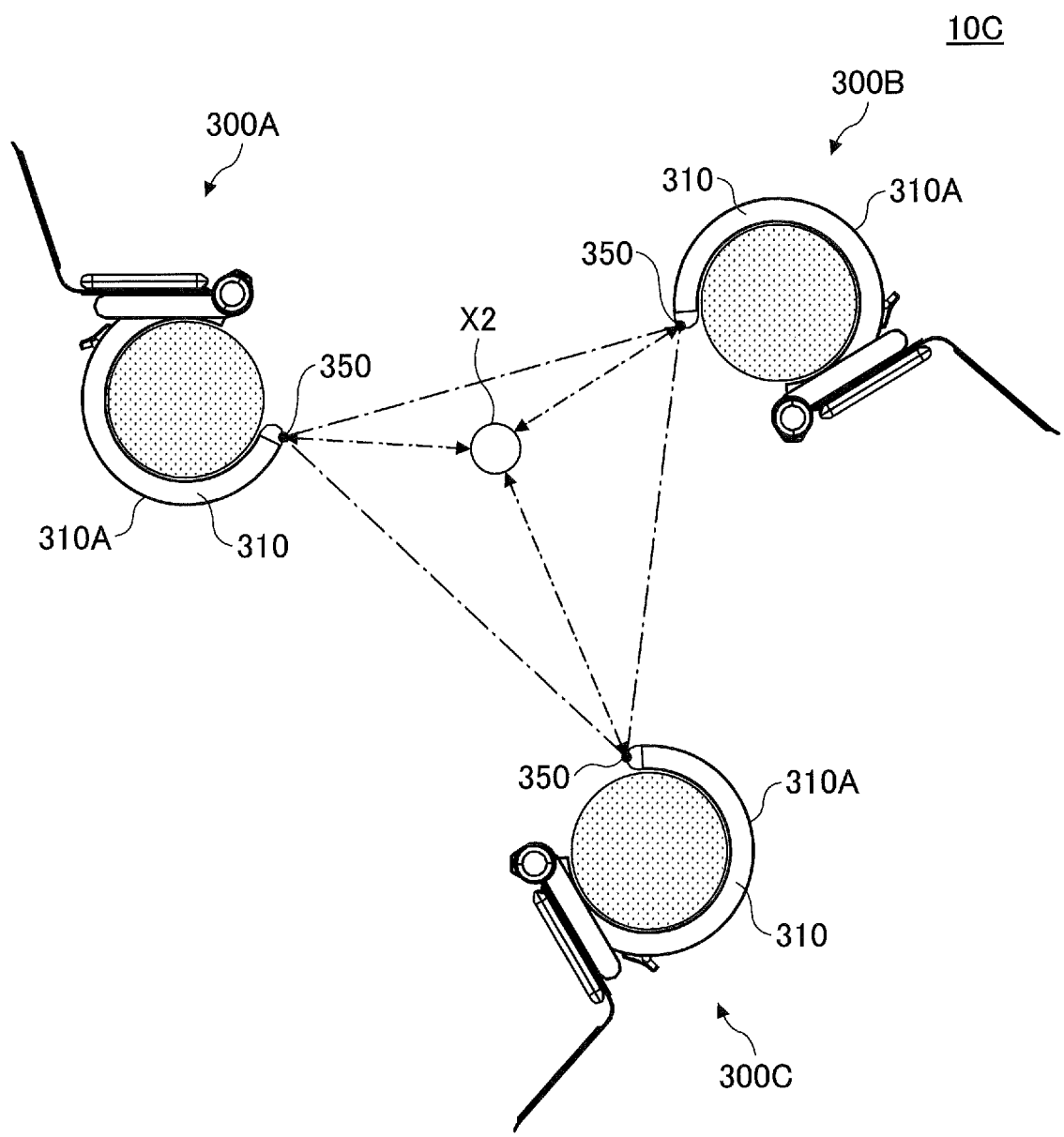
FIG. 21 illustrates a configuration of a system according to a second embodiment.

FIG. 21 illustrates a system 10C according to a second embodiment. The system 10C includes cassettes 300A, 300B, and 300C. Each of the cassettes 300 includes a sensor 350 at the front end of the housing 310. The sensor 350 is an example of a "second sensor module" whose sensing direction faces outward from the housing 310, and measures the distance to an object located outside of the cassette 300. The sensor 350 may be implemented by a Doppler sensor, an infrared sensor, or an ultrasonic sensor. The position of the sensor 350 is not limited to the front end, but the sensor 350 is preferably disposed in a portion other than the wall 310A, to prevent the position of the sensor 350 from being moved as a result of opening or closing the wall 310A. Each cassette 300 includes a second acquirer that obtains a detection value of the sensor 350 and a second output controller that outputs the detection value obtained by the second acquirer to the terminal 100. The second acquirer and the second output controller may be implemented by the processor 307.

In FIG. 21, three cassettes 300 are disposed to surround an object X2. Each of the cassettes 300 can measure a distance to the object X2 by using the sensor 350. In the system 10C, one of the cassettes 300 detects the position of the object X2 based on the positions of the cassettes 300 and obtained detection values of the sensors 350. In the system 10C, the three cassettes 300 may perform intergroup communication and cooperate with each other to detect the position of the object X2. In this case, one of the cassettes 300 functions as a master, and the other two cassettes 300 function as slaves in the intergroup communication. The master cassette 300 measures the distance from itself to the object X2, requests the slave cassettes 300 to measure distances from the slave cassettes 300 to the object X2, and collects distance data measured by the slave cassettes 300. Then, the master cassette 300 calculates the position of the object X2 by triangulation based on the distance measured by the master cassette 300 and collected from the slave cassettes 300, and the position of the three cassettes 300. The positions of the cassettes 300 may be predetermined or may be measured by the cassettes 300 using, for example, the Global Positioning System (GPS).

Third Embodiment

Figure 22:
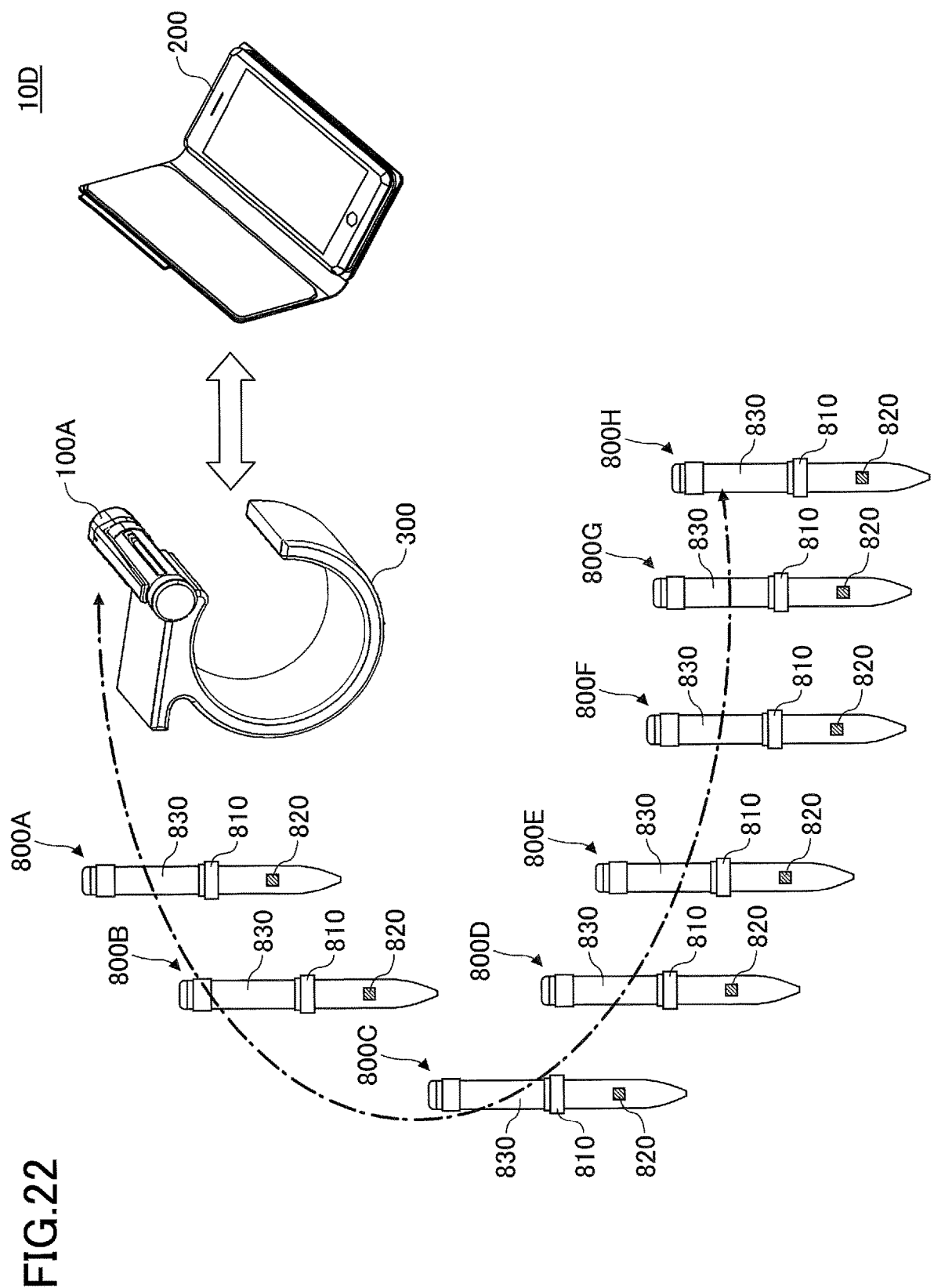
FIG. 22 illustrates a configuration of a system according to a third embodiment.

FIG. 22 illustrates a system 10D according to a third embodiment. The system 10D includes a terminal 100A, a cassette 300, and eight sensor units 800A through 800H. Each of the eight sensor units 800 has a pen shape and includes a power source 830, a switch 810, and a sensor module 820. The power source 830 and the switch 810 have substantially the same configurations as the power source 113 and the switch 130 of the terminal 100. The sensor module 820 has substantially the same function as the sensor module 320. However, in the third embodiment, the sensor included in the sensor module 320 and the sensor module 820 are not limited to light emitters, and any types of sensors may be used depending on items to be measured.

In the system 10D, the cassette 300 performs measurement using the sensor modules 320. Each sensor unit 800 performs measurement using the sensor module 820 and outputs the measurement result via the BLE communication. In the system 10D, the terminal 100A and the sensor units 800 perform data linkage via intergroup communication so that sensor data obtained by the eight sensor units 800 and the sensor data obtained by the cassette 300 can be aggregated by the terminal 100A, printed using the printer 120, and transmitted to the smartphone 200 via BLE communication.

Figure 23:
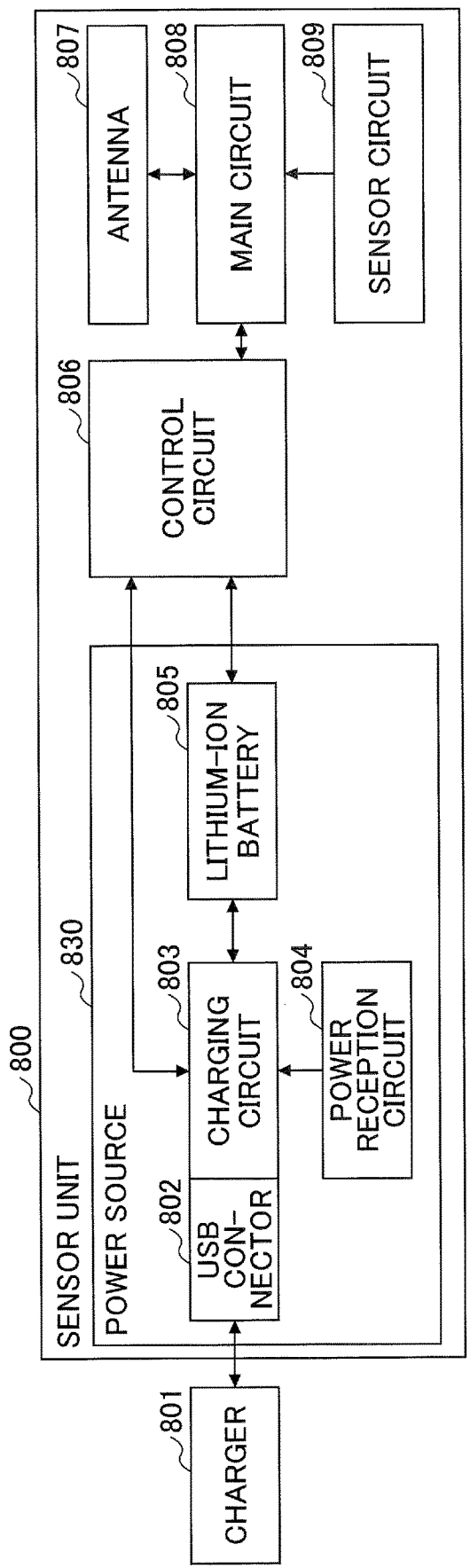
FIG. 23 is a block diagram illustrating a hardware configuration of a sensor unit.

FIG. 23 illustrates a block diagram of the sensor unit 800. The power source 830 includes a USB connector 802, a charger 803, a receiver 804, and a lithium-ion battery 805. A charger 801 is connected to the USB connector 802 to supply power to the charger 803. The receiver 804 contactlessly receives power and supplies the received power to the charger 803. The charger 803 charges the battery 805 with the power supplied from the charger 801 or the receiver 804.

The sensor unit 800 includes a controller 806, an antenna 807, a main circuit 808 with a BLE controller, and a sensor circuit 809. The controller 806 performs a control process according to instructions input via the switch 810. The antenna 807 transmits and receives radio waves. The main circuit 808 controls the sensor unit 800 and the BLE communications. The sensor circuit 809 controls the sensor module 820.

Figure 24:
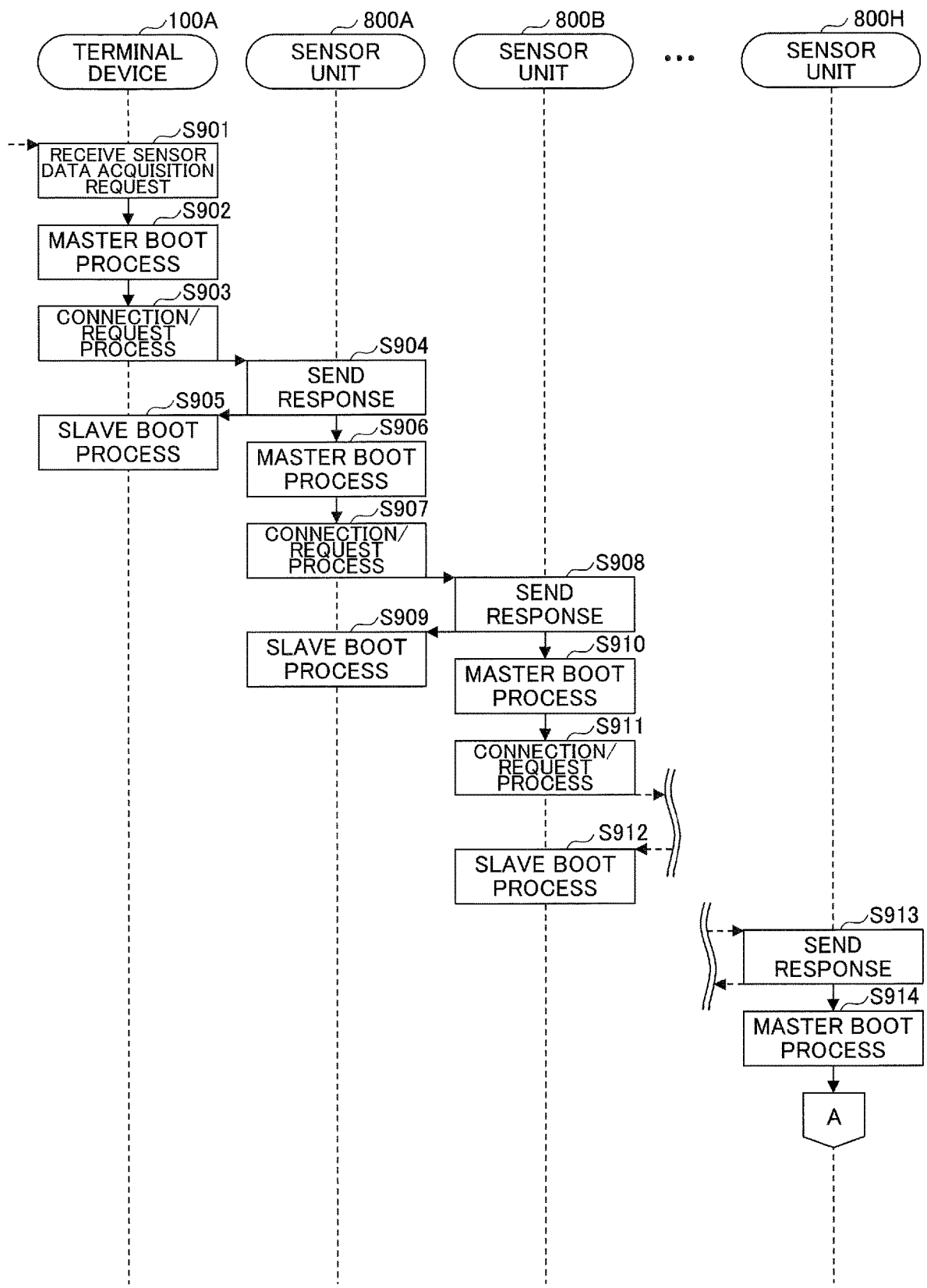
FIGS. 24 and 25 are sequence charts illustrating a data collection process according to the third embodiment.
Figure 25:
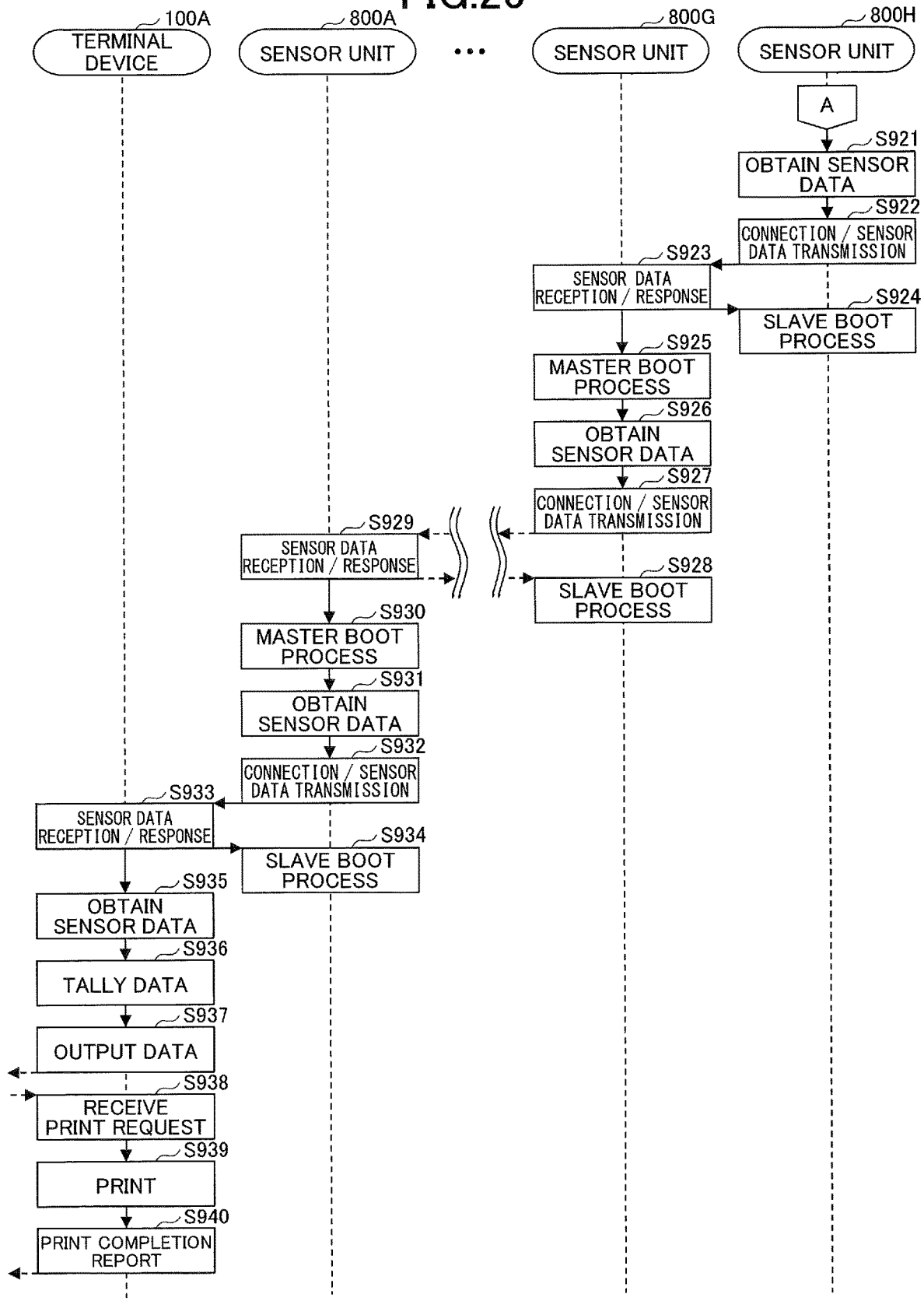

FIGS. 24 and 25 are sequence charts illustrating a collection process performed by the system 10D. A master-mode reboot process performed by the terminal 100A and the sensor units 800 includes setting a master-switching request flag, a WDT (watchdog timer) stop process, and a master-mode boot process. A slave-mode reboot process performed by the terminal 100A and the sensor units 800 includes setting a slave-switching request flag, a WDT stop process, and a slave-mode boot process.

When the terminal 100A receives an acquisition request from the smartphone 200 (S901), the terminal 100A reboots in the master mode (S902). Then, the terminal 100A establishes a BLE communication connection with the sensor unit 800A, and transmits the acquisition request to the sensor unit 800A (S903).

The sensor unit 800A transmits a response to the acquisition request to the terminal 100A (S904). Upon receiving the response, the terminal 100A reboots in the slave mode (S905), and the sensor unit 800A reboots in the master mode (S906). Then, the sensor unit 800A establishes a BLE communication connection with the sensor unit 800B, and transmits an acquisition request to the sensor unit 800B (S907).

The sensor unit 800B transmits a response to the acquisition request to the sensor unit 800A (S908). Upon receiving the response, the sensor unit 800A reboots in the slave mode (S909), and the sensor unit 800B reboots in the master mode (S910). Then, the sensor unit 800B establishes a BLE communication connection with the sensor unit 800C, and transmits an acquisition request to the sensor unit 800C (S911).

Similarly, each of the sensor units 800C through 800G transmits a response to the acquisition request to the higher sensor unit 800, reboots in the master mode, establishes a BLE communication connection with the lower sensor unit 800, and transmits an acquisition request to the lower sensor unit 800.

When the sensor unit 800G establishes a BLE communication connection with the lowest sensor unit 800H and transmits an acquisition request to the sensor unit 800H, the sensor unit 800H transmits a response to the acquisition request to the sensor unit 800G (S913), reboots in the master mode (S914), and then proceeds to S921.

The sensor unit 800H obtains sensor data from its own sensor module 820 (S921). Then, the sensor unit 800H establishes a BLE communication connection with the sensor unit 800G and transmits the sensor data to the sensor unit 800G (S922). Here, it is assumed that the sensor unit 800H is set as a terminal in advance.

The sensor unit 800G transmits a response to the reception of the sensor data to the sensor unit 800H (S923). Upon receiving the response, the sensor unit 800H reboots in the slave mode (S924). The sensor unit 800G reboots in the master mode (S925) and obtains sensor data from its own sensor module 820 (S926). The sensor unit 800G establishes a BLE communication connection with the sensor unit 800F and transmits its own sensor data and the sensor data from the sensor unit 800H to the sensor unit 800F (S927).

Similarly, each of the sensor units 800F through 800B transmits a response to the reception of the sensor data to the lower sensor unit 800 and reboots in the master mode. Then, each of the sensor units 800F through 800B obtains sensor data from its own sensor module 820, establishes a BLE communication connection with the higher sensor unit 800, and transmits its own sensor data and the sensor data received from the lower sensor unit 800 to the higher sensor unit 800.

Accordingly, the sensor unit 800B transmits the sensor data of the sensor units 800B through 800H to the highest sensor unit 800A.

The sensor unit 800A transmits a response to the reception of the sensor data to the sensor unit 800B (S929). Then, the sensor unit 800A reboots in the master mode (S930) and obtains sensor data from its own sensor module 820 (S931). The sensor unit 800A establishes a BLE communication connection with the terminal 100A, and transmits its own sensor data and the sensor data received from the sensor unit 800B to the terminal 100A (S932). Accordingly, the sensor data of the sensor units 800A through 800H is transmitted to the terminal 100A.

The terminal 100A transmits a response to the reception of the sensor data to the sensor unit 800A (S933). Upon receiving the response, the sensor unit 800A reboots in the slave mode (S934). The terminal 100A obtains sensor data from the sensor modules 320 of the cassette 300 connected to the terminal 100A via BLE communication (S935). Then, the terminal 100A tallies the sensor data from own sensor modules 320 and the sensor data of the sensor units 800A through 800H (S936), and outputs the tallying result to the smartphone 200 (S937).

Thereafter, when receiving a print request for printing the sensor data from the smartphone 200 (S938), the terminal 100A prints the tallying result (S939), and transmits a print completion report to the smartphone 200 (S940).

In the third embodiment, the terminal 100A can obtain the sensor data of the sensor modules 320 and of the respective sensor units 800, transmit the sensor data to the smartphone 200, and print the sensor data using the printer 120. In the third embodiment, it is possible to tally, transmit, and print measurement data obtained at nine measurement positions.

In the third embodiment, a communication path is formed such that multiple sensor units 800 are connected in series to the terminal 100A functions as the highest node. In the communication path, pairs of adjacent sensor units 800 sequentially perform BLE communications from the lower end toward the upper end. In each pair, the lower sensor unit 800 transmits sensor data including own sensor data to the higher sensor unit 800. As a result, the sensor data are aggregated at the highest terminal 100A. According to this method, the maximum distance between the terminal 100A and the lowest sensor unit 800 can be set at {(number of sensor units −1)×maximum BLE communication distance}, and measurement at multiple positions is performed in a comparatively large area.

Figure 26:
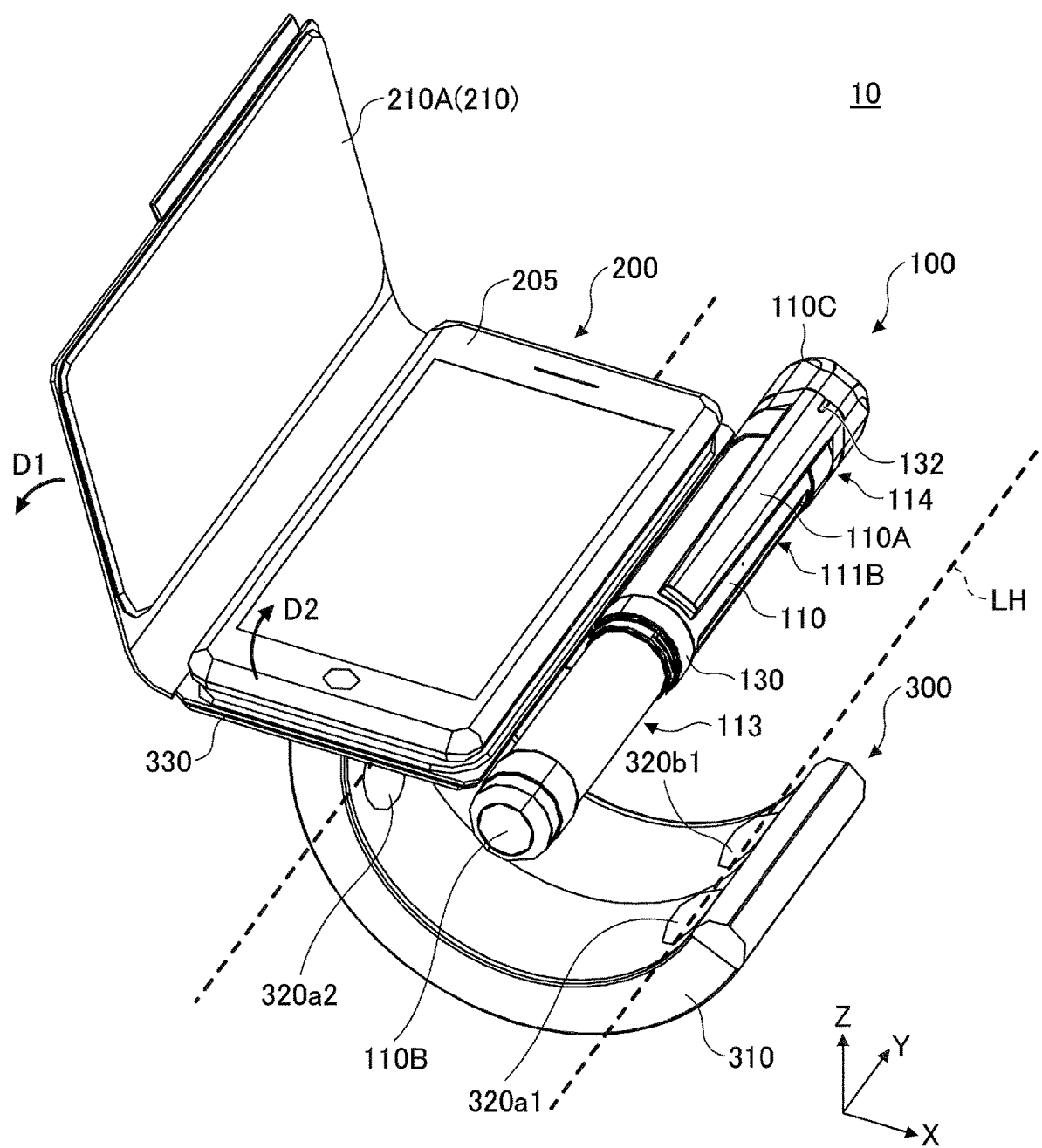
FIG. 26 illustrates an arrangement of a smartphone and a terminal.
Figure 27:
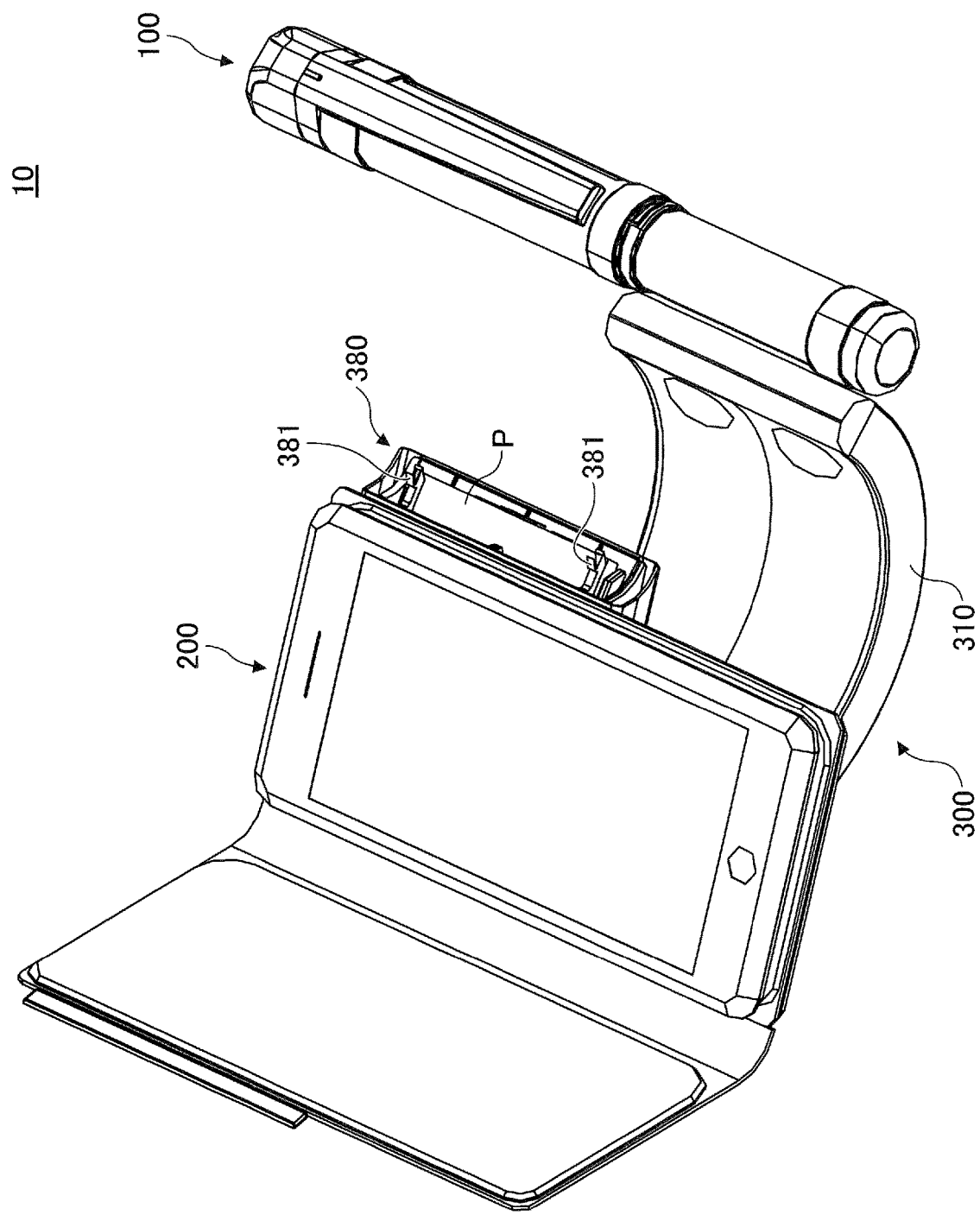
FIGS. 27 and 28 are perspective views of the terminal is detached from the cassette.
Figure 28:
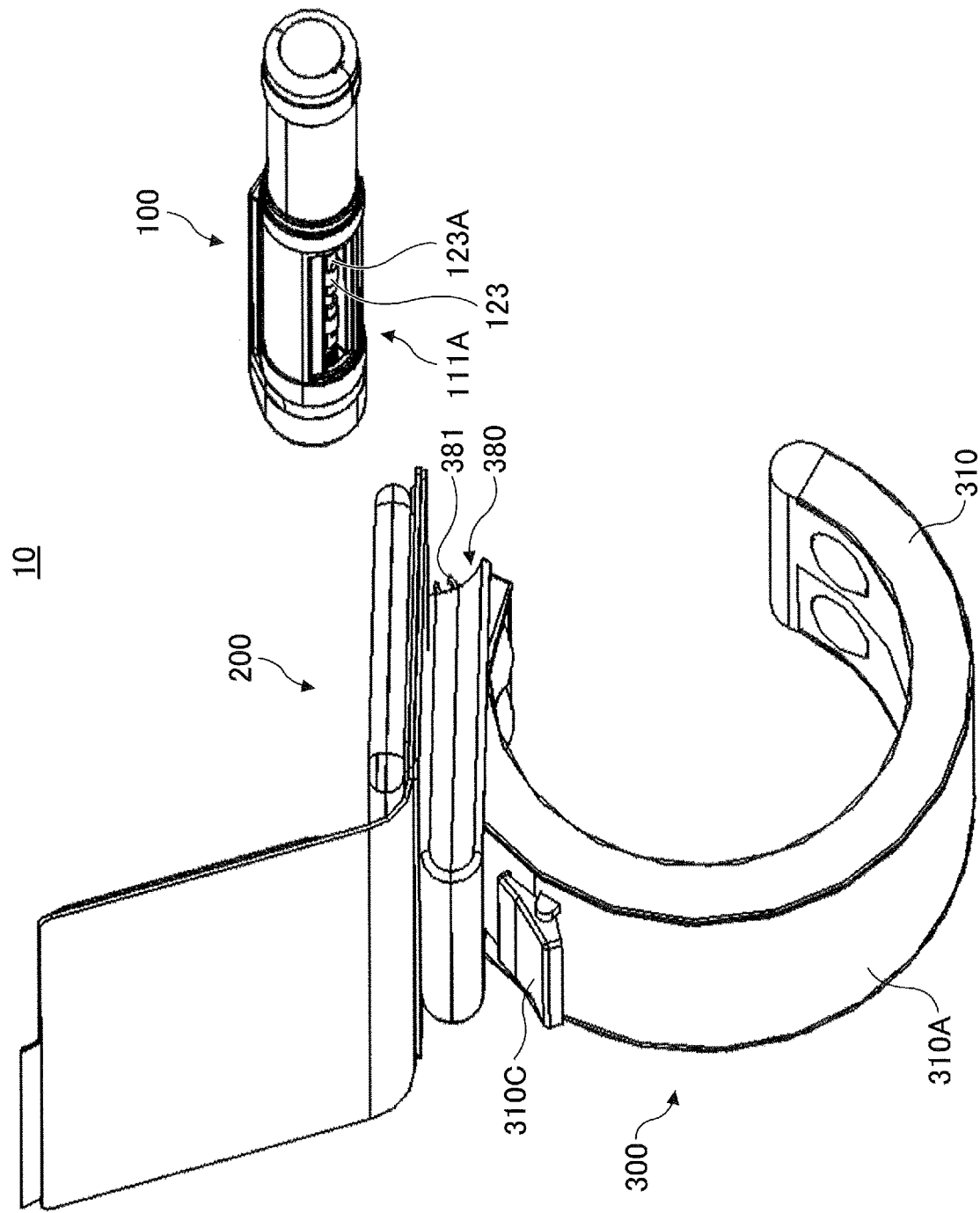

FIG. 26 illustrates an arrangement of the smartphone 200 and the terminal 100. Each sensor module 320 includes biosensors, and the housing 310 can be attached to a left arm LH of a user to detect user's biological information such as a body temperature, a pulse, a heart rate, and a sweat rate. As illustrated in FIG. 26, when the cassette 300 is attached to the arm LH such that the opening of the housing 310 faces the right side (+X side), the smartphone 200 is preferably mountable on the table 330 such that the lower side of a body 205 is located closer to the joint (−Y end) of the arm LH. Also, a cover 210A of a jacket 210 is preferably rotatable outward in a D1 direction around a rotational axis that is near a left edge (−X edge) of the body 205. The cover 210A can be easily opened outward to view information displayed on the smartphone 200 and to operate the smartphone 200 with the right hand. Also, the terminal 100 is preferably disposed on the right side of the smartphone 200 such that the discharge port 111B faces the right side, to make easier for the user to operate the switch 130 with the right hand and to view and remove the paper P discharged from the discharge port 111B. The table 330 may include an adjuster for adjusting the angle of the table 330 such that the surface of the body 205 faces inward as indicated by an arrow D2 in FIG. 26. The housing 310 may has an inside diameter corresponding to the size and shape of an object to be measured.

Figure 29:
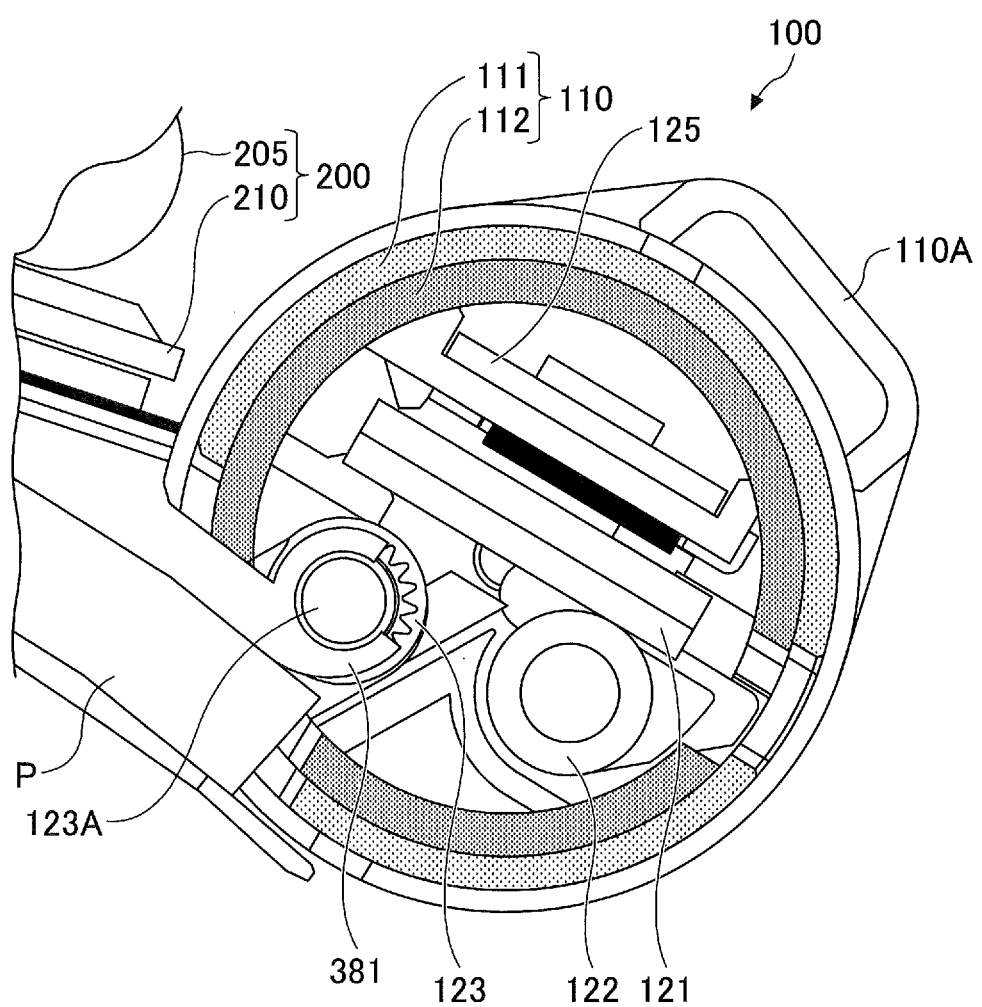
FIG. 29 is a cross-sectional view of a connector.

FIGS. 24 and 25 are perspective views of the system 10 where the terminal 100 is separated from the cassette 300. FIG. 26 is a cross-sectional view of the connector 380. The connector 380 is provided at the right edge of the body 305. The connector 380 has an opening for feeding paper and is detachably attached to the feed port 111A. With the connector 380 connected to the feed port 111A, the paper P stored in the housing 310 can be supplied to the printer 120. The feed roller 123 and a shaft 123A for supporting the feed roller 123 are exposed through the feed port 111A. Clips 381 projecting toward the terminal 100 are provided in the connector 380. As illustrated in FIG. 29, when the connector 380 is connected to the terminal 100, the shaft 123A is fitted into and held by the clips 381 to maintain the connection between the cassette 300 and the terminal 100.

<Variations>

Figure 30:
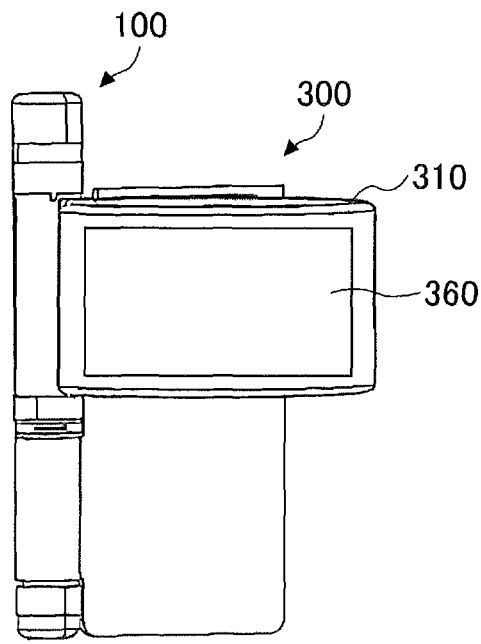
FIGS. 30 and 31 illustrate variations of a cassette.
Figure 31:
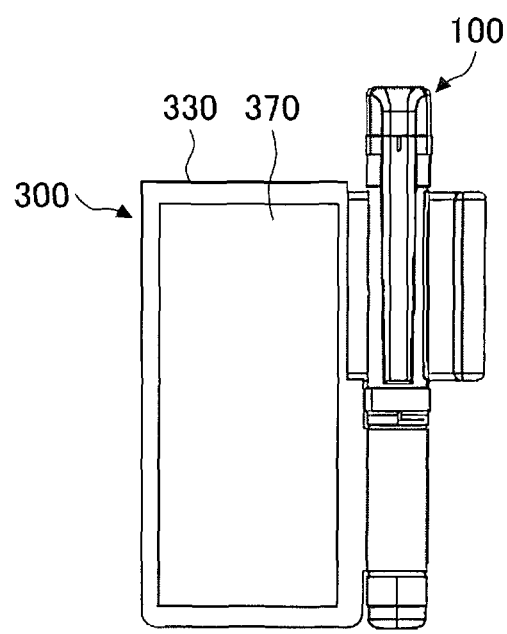

FIGS. 30 and 31 illustrate variations of the cassette 300. In FIG. 30, a touch panel 360 is provided on the housing 310. The touch panel 360 displays information and enables the user to perform operations. In FIG. 31, a solar panel 370 is provided on the table 330 so that the battery 426 can be charged with the solar panel 370. Various sensors such as an angle sensor and a high-precision sensor may be provided on the table 330.

As described above, according to the present embodiment, an object can be measured using multiple sensor modules 320 and print the measurement results by connecting the connector 380 to the terminal 100. As the cassette 300 is integrated with the sensor modules 320 and can also be connected to the printer 120, these devices can be easily connected and carried. The cassette 300 can be attached to an object while integrated with the above devices. The sensor modules 320 can measure various states in a space surrounded by the housing 310 from multiple directions. Thus, the cassette 300 can perform measurements according to the types of sensors in the sensor modules 320. Accordingly, the cassette 300 can implement a terminal device that performs measurement and printing and can be easily handled.

<Other Variations>

The housing 310 may have a first portion on the outer surface side and houses the paper P, and a second portion on the inner surface side on which the sensor modules 320 are mounted and is detachably attached to the first portion.

In the above embodiment, three sensor modules 320 are arranged on the inner surface of the housing 310. However, four or more sensor modules 320 may be arranged.

Three openings 340D are formed in the housing 310 in the above embodiment. However, four or more openings 340D may be arranged. In this case, the sensor modules 320 may be provided in all of the openings 340D or may be provided in three or less of the openings 340D selected.

In the above embodiment, two sensor groups are provided on the housing 310. However, three or more sensor groups may be provided.

The sensor included in the sensor module 320 is not limited to a light receiver but may be any sensor that is suitable for an item to be measured. For example, each sensor module 320 may include biosensors to detect biological information.

The sensor modules 320 may include distance sensors. The distance sensors on the first plane f1 may detect distances to and the position of the object on the first plane f1. Similarly, the distance sensors on the second plane f2 may detect distances to and the position of the object on the second plane f2. The moving speed and the moving direction of the object can be calculated based on the detected position of the object, and the times at which the positions of the object are detected.

The sensor modules 320 may include temperature sensors. The temperature sensors on the first plane f1 may detect temperatures on the first plane f1 and an average of the temperatures may be calculated. Similarly, the temperature sensors on the second plane f2 may detect temperatures on the second plane f2 and an average of the three detected temperatures may be calculated. A temperature gradient may be calculated based on the average temperatures.

The terminal 100 receives print data from the smartphone 200 or another terminal 100, and prints the received print data. Even when the terminal 100 is not connected to other devices, the terminal 100 can print data stored in a memory.

The terminal 100 forms a group with one or more devices such as smartphones, and performs intergroup communication with the devices. The terminal 100 may function as a master, and the other devices may function as slaves. Alternatively, one of the other devices may function as a master, and the terminal 100 may function as a slave. The terminal 100 shares data with the other devices through the intergroup communication.

The terminal 100 may form a group with one or more other terminals and perform intergroup communication. The terminal 100 may function as a master and the other terminals may function as slaves. The terminal 100 can share data with the other terminals through the intergroup communication. Each other terminal may have functions similar to the terminal 100 such as printing and intergroup communication. Also, each other terminal may perform intergroup communication with a smartphone and can function as a master.

The terminal 100 may form a group with one or more sensors, and perform intergroup communication with the sensors. The terminal 100 may function as a master, and the sensors may function as slaves. The terminal 100 obtains detection data indicating temperatures, pressures, positions, and/or acceleration from the sensors through the intergroup communication. The terminal 100 stores the detection data in a memory or prints the detection data with the printer 120. The terminal 100 can output the detection data to the smartphone 200, or share the detection data with other terminals 100.

The terminal 100 can reduce the amount of data to be communicated with other devices constituting a group by using context data having a predetermined data structure and objects shared among multiple devices.

The library may store objects with corresponding object identifiers, and position information with corresponding position identifiers. The terminal 100 receives from the smartphone 200 context data to which an object identifier identifying a printing object and a position identifier identifying a printing position are set. The terminal 100 identifies the printing object and the printing position based on the received context data. The terminal 100 synchronizes its library with the smartphone 200 beforehand so that the printing object is held in own library. Accordingly, the terminal 100 can print the object stored in own library without receiving from the smartphone 200.

The terminal 100 can synchronize libraries for storing objects among devices forming a group with the terminal 100. The terminal 100 may synchronize libraries with the other devices by transmitting own local objects to the other devices to store in their libraries, or storing the objects received from the other devices in its own library.

The terminal 100 can combine multiple objects for a common application that are collected using context data from other devices within the group, and transmit the combined objects to the other devices using context data. As a result, the devices within the group can share, display, and print the same data.

Various expansion units may be attached to the terminal 100. A pen-tip unit with a writing tool may be attached to the terminal 100 to handwrite comments on papers or labels attached to a scrapbook or a notebook using the terminal 100.

A laser pointer including a laser unit and an aperture through which a laser beam is emitted may be attached to the terminal 100. With the laser pointer attached to the terminal 100, the user can point to a target on a white board with the laser beam. The laser pointer is electrically connected to the terminal 100, and can be controlled by operating the switch 130.

A touch-pen type sensor unit 800 may be attached to the power source 113. The sensor unit 800 is driven by power from the power source 113. The touch panel of the smartphone 200 can be touched with a tip of the sensor unit 800. Another expansion unit may be attached to the other end of the power source 113.

The terminal 100 can print an object on a label sheet. The user can attach the printed label sheet to a notebook. Label sheets with different sizes may be used by changing cassettes 300 or by replacing a label sheet in the cassette 300. If the cassette 300 can store label sheets with different sizes, one of the label sheets can be selected.

The terminal 100 may include a switcher for switching the operation modes of the terminal 100 between the master mode and the slave mode. The switcher may switch the operation modes according to an operation of the switch 130. The terminal 100 may be configured to operate in the slave mode as a default and to be switched to the master mode by the switcher when the switch 130 is operated. The operation mode of the terminal 100 is maintained even when the power is turned off. When the power is turned off while the terminal 100 is in the master mode, the terminal 100 boots in the master mode when the power is turned on again. When the power is turned off while the terminal 100 is in the slave mode, the terminal 100 boots in the slave mode when the power is turned on again. If a power-off operation is performed while a mode switching process is being executed, the terminal 100 temporarily maintains the power-on state for an initialization process for the mode switching process instead of immediately turning off the power. While the power-on state is maintained, the terminal 100 securely switches the operation modes and reports the completion of the switching operation to the user using an indicator 132, and then turns off the power. The master/slave switching may also be performed in response to a switching command from a higher node.

The terminal 100 may include a data collector, a data generator, and a data distributor for intergroup communication. When the terminal 100 is in the master mode, the data collector collects application data using context data from slave terminal 100. The data collector may collect data for a print application or an SNS application. The data generator generates data for the application from the collected application data. The data distributor distributes data to the slave terminals.

The terminal 100 includes a management unit that manages a management table for intergroup communication storing, for each group, a group ID and IDs of users allowed to join the group. The user of the master terminal 100 can operate the switch 130 to select a group to be used for intergroup communication. Then, the master terminal 100 connects to other devices belonging to the selected group to establish the group.

A cassette and a system according to the embodiments are described above. However, the present invention is not limited to the specifically disclosed embodiments.

What is claimed is:

1. A cassette connectable to a printer, the cassette comprising:
   a housing configured to house a recording sheet;
   a connector that is connected to a feed port of the printer for supplying the recording sheet to the printer; and
   a sensor group including sensor modules that measure a state in a space surrounded by the housing, wherein
   the housing has an arc shape; and
   sensor groups are arranged apart from each other in a direction intersecting a circumferential direction of an inner surface of the housing.

2. A cassette connectable to a printer, the cassette comprising:
   a housing configured to house a recording sheet;
   a connector that is connected to a feed port of the printer for supplying the recording sheet to the printer; and
   a sensor group including sensor modules that measure a state in a space surrounded by the housing, wherein
   the housing has an arc shape;
   sensor groups are arranged apart from each other in a direction intersecting a circumferential direction of an inner surface of the housing;
   the housing includes an arm that is slidable in the circumferential direction of the inner surface; and
   at least one of the sensor groups is disposed on the arm.

3. A cassette connectable to a printer, the cassette comprising:
   a housing configured to house a recording sheet;
   a connector that is connected to a feed port of the printer for supplying the recording sheet to the printer;
   a sensor group including sensor modules that measure a state in a space surrounded by the housing; and
   a wiring disposed inside of the housing, wherein
   the wiring includes different connection patterns corresponding to positions of the openings;
   each sensor module includes position detection terminals; and
   the sensor module determines a position of the sensor module based on a combination of the position detection terminals that are electrically connected to any of the connection patterns.

4. The cassette as claimed in claim 1, wherein
each of the sensor modules includes a light emitter and a light receiver; and
the cassette further comprises
- an emission controller that emits the light emitters of a first sensor modules,
- an acquirer that obtains signal from light receivers of a second sensor modules other than the first sensor modules, and
- a determiner that determines a state of an object between two sensor modules based on the signal from the light receivers.

5. A system, comprising:
a terminal device; and
the cassette as claimed in claim 1.

6. The system according to claim 5, further comprising:
multiple sensor units each of which includes a sensor and a wireless communicator, wherein
the terminal device, the cassette, and the sensor units are connected in series as nodes to form a communication path where the terminal device, the cassette, or one of the sensor units functions as a highest node;
adjacent pairs of the nodes sequentially perform wireless communications in a downward or an upward direction in the communication path;
in each of the adjacent pairs of the nodes, a lower node transmits to a higher node, data obtained by the lower node and data received from a node located lower than the lower node; and
the highest node aggregates the data obtained by the nodes in the communication path.

\* \* \* \* \*